(12) United States Patent
Bassler et al.

(10) Patent No.: US 9,968,587 B2
(45) Date of Patent: May 15, 2018

(54) HETEROCYCLE ANALOGS OF CAI-1 AS AGONISTS OF QUORUM SENSING IN VIBRIO

(71) Applicant: THE TRUSTEES OF PRINCETON UNIVERSITY, Princeton, NJ (US)

(72) Inventors: Bonnie L. Bassler, Princeton, NJ (US); Lark J. Perez, Ewing, NJ (US); Martin F. Semmelhack, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days. days.

(21) Appl. No.: 14/912,207

(22) PCT Filed: Aug. 19, 2014

(86) PCT No.: PCT/US2014/051648
§ 371 (c)(1),
(2) Date: Feb. 16, 2016

(87) PCT Pub. No.: WO2015/026796
PCT Pub. Date: Feb. 26, 2015

(65) Prior Publication Data
US 2016/0200678 A1 Jul. 14, 2016

Related U.S. Application Data

(60) Provisional application No. 61/867,831, filed on Aug. 20, 2013.

(51) Int. Cl.
| | | |
|---|---|---|
| A61K 31/401 | (2006.01) |
| A01N 43/36 | (2006.01) |
| C07D 207/333 | (2006.01) |
| A61K 45/06 | (2006.01) |
| A61K 31/53 | (2006.01) |

(52) U.S. Cl.
CPC ............ *A61K 31/401* (2013.01); *A01N 43/36* (2013.01); *A61K 31/53* (2013.01); *A61K 45/06* (2013.01); *C07D 207/333* (2013.01)

(58) Field of Classification Search
CPC .. C07D 207/333; A61K 45/06; A61K 31/401; A61K 31/53; A01N 43/36
See application file for complete search history.

(56) References Cited

U.S. PATENT DOCUMENTS

| 6,777,420 B2 | 8/2004 | Zhi et al. |
| 2010/0273890 A1 | 10/2010 | Bassler et al. |
| 2012/0322769 A1 | 12/2012 | Yang et al. |

OTHER PUBLICATIONS

Collard et al., 1994, caplus 1994:410137.*
Papireddy et al., 2011, caplus an 2011:858787.*
Preventing-a-Bacterial-Infection, 2017, http://www.wikihow.com/Prevent-a-Bacterial-Infection.*
Mai et al., 2004, caplus an 2004:61092.*
Bolli et al., 2014, caplus an 2014:618160.*
Perez et al., 2014, 5(1), 151-155.*
PuBChem-CID 65448370-Create Date: Oct. 24, 2012, p. 1.
PuBChem-CID 682135-Create Date: Jul. 8, 2005, p. 1, Figure.
Afzali-Ardakani et al., "L-Vinylglycine", J. Org. Chem., vol. 45, 1980, pp. 4817-4820.
Liu et al., "Improved syntheses of alpha-BOC-aminoketones from alpha-BOC-amino-Weinreb amides using a pre-deprotonation protocol", Tetrahedron letters, vol. 43, 2002, pp. 8223-8226.
Biraboneye et al., "Neuroprotective Effects of N-Alkyl-1,2,4-oxadiazolidine-3,5-diones and Their Corresponding Synthetic Intermediates N-Alkylhydroxylamines and N-1-Alkyl-3-carbonyl-1-hydroxyureas against in vitro Cerebral Ischemia", ChemMedChem, vol. 5, 2010, pp. 79-85.
Lenz et al., "The small RNA chaperone Hfq and multiple small RNAs control quorum sensing in Vibrio harveyi and Vibrio cholerae", Cell, vol. 118, 2004, pp. 69-82.
Higgins et al., "The major Vibrio cholerae autoinducer and its role in virulence factor production", Nature, vol. 450, 2007, pp. 883-886.
ICCVAM. 2006a. Background Review Document: In Vitro Cytotoxicity Test methods for Estimating Acute Oral Systemic Toxicity. NIH Publication No. 07-4518. Research Triangle Park, NC:National Institute of Environmental Health Sciences. Available Aug. 13, 2013: http://iccvam.niehs.nih.gov/.
NG et al., "Bacterial quorum-sensing network architectures", Annu. Rev. Genet., vol. 43, 2009, pp. 197-222.
Bassler et al. "Small talk: cell-to-cell communication in bacteria", Cell, vol. 109, 2002, pp. 421-424.
Geske et al., "Expanding dialogues: from natural autoinducers to non-natural analogues that modulate quorum sensing in Gram-negative bacteria", Chem. Soc. Rev., vol. 37, 2008, pp. 1432-1447.
Hentzer et al., "Attenuation of Pseudomonas aeruginosa virulence by quorum sensing inhibitors", The EMBO journal, vol. 22, 2003, pp. 3803-3815.
Njoroge et al., "Jamming bacterial communication: New approaches for the treatment of infectious diseases", EMBO mol. med., vol. 1, 2009, pp. 201-210.
Swem et al., "A Quorum-Sensing Antagonist Targets Both MembraneOBound and Cytoplasmic Receptors and controls Bacterial Pathogenicity", Molecular Cell, vol. 35, 2009, pp. 143-153.
Kovacikova et al., "Regulation of virulence gene expression in Vibrio cholerae by quorum sensing: HapR functions at the aphA promoter", Molecular Microbiology, vol. 46, 2002 pp. 1135-1147.
Liu et al., "Mucosal penetration primes Vibrio cholerae for host colonization by repressing quorum sensing", PNAS, vol. 105, 2008, pp. 9769-9774.
Schuster et al., "Identification, Timing, and Signal Specificity of Pseudomonas aeruginosa Quorum-Controlled Genes: a Transcriptome Analysis", Journal of Bacteriology, vol. 185, 2003, pp. 2066-2079.

(Continued)

*Primary Examiner* — Sun Jae Yoo
(74) *Attorney, Agent, or Firm* — Meagher Emanuel Laks Goldberg & Liao, LLP

(57) ABSTRACT

A structurally distinct and potent series of synthetic small molecule activators of *Vibrio cholerae* quorum sensing have been chemically synthesized. The small molecule activators reduce virulence in *V. cholerae*. Acyl pyrrole molecules displayed strong potency and stability, particularly 1-(1H-pyrrol-3-yl)decan-1-one

(56) References Cited

OTHER PUBLICATIONS

Nadell et al., "The Evolution of Quorum Sensing in Bacterial Biofilms", PLOS Biology, vol. 6, 2008, pp. 171-179.
Hammer et al., "Quorum sensing controls biofilm formation in Vibrio cholerae", Molecular Microbiology, vol. 50, 2003, pp. 101-114.
Miller et al., "Parallel Quorum Sensing Systems Converge to Regulate Virulence in Vibrio cholerae", Cell, vol. 110, 2002, pp. 303-314.
Zhu et al., "Quorum Sensing-Dependent Biofilms Enhance Colonization in Vibrio cholerae", Developmental Cell, vol. 5, 2003, pp. 647-656.
Zhu et al., "Quorum-sensing regulators control virulence gene expression in Vibrio cholerae", PNAS, vol. 99, 2002, pp. 3129-3134.
Duan et al., "Engineered bacterial communication prevents Vibrio cholerae virulence in an infant mouse model", 'PNAS, vol. 107, 2010, pp. 11260-11264.
Defoirdt et al., "The impact of mutations in the quorum sensing systems of Aeromonas hydrophila, Vibrio anguillarum and Vibrio harveyi on their virulence towards gnotobiotically cultured Anemia franciscana", Environmental Microbiology, vol. 7, 2005, pp. 1239-1247.
Gode-Potratz et al., "Quorum Sensing and Silencing in Vibrio parahaemolyticus", Journal of Bacteriology, vol. 193, 2011, pp. 4224-4237.
Roh et al., "Transcriptional Regulatory Cascade for Elastase Production in Vibrio vulnificus LuxO Activates luxT Expression and LuxT Represses smcR Expression", Journal of Biological Chemistry, vol. 281, 2006, pp. 34775-34784.
Shao et al., "Regulation of cytotoxicity by quorum-sensing signaling in Vlbrio vulnificus is mediated by SmcR, a repressor of hlyU", Journal of Bacteriology, vol. 193, 2011, pp. 2557-2565.
Wang et al., "LuxO controls extracellular protease, haemolytic activities and siderophore production in fish pathogen Vibrio alginolyticus", Journal of Applied Microbiology, vol. 103, 2007, pp. 1525-1534.
Ng et al., "Broad spectrum pro-quorum-sensing molecules as inhibitors of virulence in vibrios", PLoS Pathog., vol. 8, 2012, e10022767.
Wei et al., "Mechanism of Vibrio cholerae autoinducer-1 biosynthesis", ACS Chem. Biol., vol. 6, 2011, pp. 356-365.
Kelly et al., "The Vibrio cholerae quorum-sensing autoinducer CAI-1: analysis of the biosynthetic enzyme CqsA", Nat. Chem. Biol., vol. 5, 2009, pp. 891-895.
Henke et al., "Three parallel quorum-sensing systems regulate gene expression in Vibrio harveyi", Journal of Bacteriology, vol. 186, 2004, pp. 6902-6914.
Ng et al., "Signal production and detection specificity in Vibrio CqsA/CqsS quorum-sensing systems", Mol. Microbiol., vol. 79, 2011, pp. 1407-1417.
Ng et al., "Probing bacterial transmembrane histidine kinase receptor-ligand interactions with natural and synthetic molecules", PNAS, vol. 107, 2010, pp. 5575-5580.
Perez et al., "Role of the CAI-1 Fatty Acid Tail in the Vibrio cholerae Quorum Sensing Response", J. Med. Chem., vol. 55, 2012, pp. 9669-9681.
Bolitho et al., "Small molecule probes of the receptor binding site in the Vibrio cholerae CAI-1 quorum sensing circuit", Bioorg. Med. Chem., vol. 19, 2011, pp. 6906-6918.
Meanwell, "Synopsis of some recent tactical application of bioisosteres in drug design", J. Med. Chem., vol. 54, 2011, pp. 2529-2591.
Ferenczy et al., "Thermodynamics guided lead discovery and optimization", Drug Discov. Today, vol. 15, 2010, pp. 919-932.
Freire, "Do enthalpy and entropy distinguish first in class from best in class?", Drug Discov. Today, vol. 13, 2008, pp. 869-874.
Fuqua et al., "Census and Consensus in Bacterial Ecosystems: The LuxR-LuxI Family of Quorum-Sensing Transcriptional Regulators", Annu. Rev. Microbial., vol. 50, 1996, pp. 727-751.
Waters et al., "Quorum sensing: cell-to-cell communication in bacteria", Annu. Rev. Cell Dev. Biol., vol. 21, 2005, pp. 319-346.
Cegelski et al., "The biology and future prospects of antivirulence therapies", Nat. Rev. Micro., vol. 6, 2008, pp. 17-27.
Clatworthy et al., "Targeting virulence: a new paradigm for antimicrobial therapy", Nat. Chem. Biol., vol. 3, 2007, pp. 541-548.
Rasko et al., "Anti-virulence strategies to combat bacteria-mediated disease", Nature reviews Drug discovery, vol. 9, 2010, pp. 117-128.
Smith et al., "P. aeruginosa quorum-sensing systems and virulence", Current Opinion in Microbioloogy, vol. 6, 2003, pp. 56-60.
Genet et al., "A General and Simple Removal of the Allyloxycarbonyl Protection Group by Palladium-catalyzed Reactions Using Nitrogen and Sulfur Nucleophiles", Synlett, vol. 1993, 1993, pp. 680-682.
Bourbeau et al., "A convenient synthesis of 4-alkyl-5-aminoisoxazoles", Org. Lett., vol. 8, 2006, pp. 3679-3680.
International Search Report for PCT/US2014/051648, dated Jan. 12, 2015.

* cited by examiner

| | EC$_{50}$ (nM) | % Inhibition |
|---|---|---|
|  18 | 13.3[a] | 91%[a] |
|  17 | 5160[a] | 91%[a] |
|  19 | 679[a] | 64%[a] |
|  20 | 536[a] | 62%[a] |
|  56 | 409 | 82% |
|  57 | >50000 | 18%[b] |

HETEROCYCLE ANALOGS OF CAI-1 AS AGONISTS OF QUORUM SENSING IN VIBRIO

CROSS-REFERENCE TO RELATED APPLICATIONS

This application claims priority to U.S. Provisional Application No. 61/867,831, filed Aug. 20, 2013, which is herein incorporated by reference in its entirety.

STATEMENT REGARDING FEDERALLY SPONSORED RESEARCH OR DEVELOPMENT

This invention was made with government support under National Institutes of Health (NIH) grants R01 AI 054442 and R01 GM 065859, and National Science Foundation (NSF) grant MCB-0948112. The government has certain rights in this invention.

BACKGROUND

Quorum sensing (QS) is a process of bacterial cell-cell communication that allows populations of bacteria to act like multicellular organisms by carrying out tasks in synchrony. The process involves secreted signaling molecules called autoinducers that the bacteria produce and release. Specifically, autoinducers accumulate at high cell densities, and when the concentration reaches a critical level, their detection drives synchronous group-wide changes in gene expression.

QS controls collective behaviors including bioluminescence, sporulation, biofilm formation, and virulence factor production. Quorum sensing plays a vital role in the pathogenicity of many bacteria because the ability to act as a coordinated group is essential for bacteria to successfully infect host organisms. Modulation of either the production or the detection of autoinducer molecules can abolish bacterial communication and render bacteria non-pathogenic.

The primary QS autoinducer in *V. cholerae* is known as CAI-1, which is the small molecule (S)-3-hydroxytridecan-4-one. CqsA synthase produces CAI-1 and CqsS is a membrane-spanning receptor that detects CAI-1. *V. cholerae* use a CqsA/CqsS quorum sensing circuit to control the production of virulence factors and require repression of this quorum sensing system to establish an infection in its host.

Typically in pathogenic bacteria that cause persistent infection, the accumulation of autoinducers at high cell densities triggers QS-mediated virulence factor production and biofilm formation. By contrast, *Vibrio cholerae*, which causes the acute intestinal disease cholera, displays an unusual QS profile: at high population density, QS initiates a cascade that suppresses virulence factor production (PCT/US2013/026837).

The distinct QS behavior exhibited by *V. cholerae* is attributed to its life cycle. Successful infection by *V. cholerae* leads to profuse diarrhea, which washes huge numbers of bacteria from the human intestine into the environment. Thus, at low cell density, the expression of genes for virulence and biofilm formation promotes establishment of infection in the host, while at high cell density, autoinducer-dependent repression of these traits promotes dissemination.

Several other clinically relevant bacteria are known to use a CqsA/CqsS quorum sensing circuit (e.g., *V. parahaemolyticus* and *V. vulnificus*). A homologous quorum sensing circuit identified in certain bacteria uses homologs of CqsA and CqsS found in e.g., *Legionella* species and in *Nitrococcus mobilis*, *Burkholderia xenovorans*, and *Polaromonas* spp.

SUMMARY OF THE INVENTION

Disclosed herein are novel strategies directed at the activation of quorum sensing in *Vibrio* species, thereby inhibiting the virulence of these bacteria and diminishing the likelihood of infection. Small-molecule modulators of quorum sensing pathways represent promising lead compounds en route to novel anti-bacterial therapeutics.

The invention encompasses the prevention, inhibition and control of bacterial diseases, including, but not limited to infections caused by *Vibrio* species and *Legionella* species. For this reason, the novel strategies described herein that activate quorum sensing in *V. cholerae*, thereby inhibiting its virulence and diminishing infection, have a broad range of clinical applications. The strategies may be applied, as well, to environmental applications such as affecting biofilms.

In a first aspect, the invention is a compound from the group consisting of:

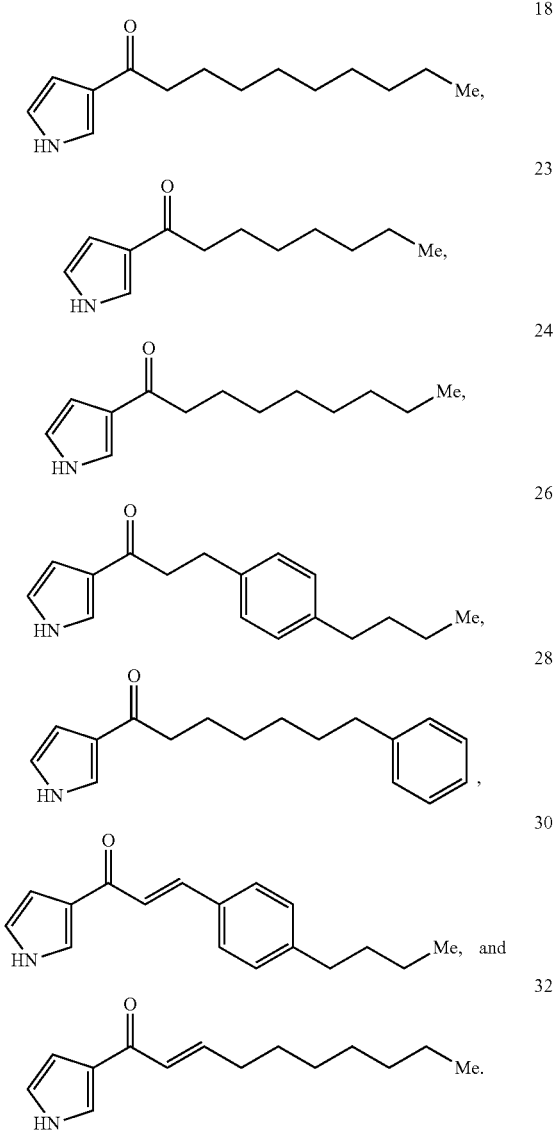

In a second aspect, the invention is a pharmaceutical composition comprising one or more of the inventive pyrrole compounds and a pharmaceutically acceptable carrier, excipient or diluent.

In another aspect, the invention is a method of treating a bacterial infection of Gram-negative quorum sensing bacteria, comprising administering to a subject a therapeutically effective amount of one or more of the inventive pyrrole compounds. The bacteria have a cholera-type QS circuit. One embodiment is directed to prophylactic treatment prior to bacterial infection. Another embodiment is directed to active treatment of bacterial infection. Yet another embodiment comprises administering to the subject a therapeutically effective amount of one or more of the inventive pyrrole compounds and an antibiotic. Still another embodiment comprises administering to the subject a therapeutically effective amount of one or more of the inventive pyrrole compounds and one or more LuxO inhibitory molecules. LuxO inhibitory molecules inhibit bacterial virulence by a mechanism that is different from that of the pyrrole compounds of the present invention. LuxO inhibitory molecules are described in PCT Application No. PCT/US2013/026837. Examples of the LuxO inhibitory molecules are:

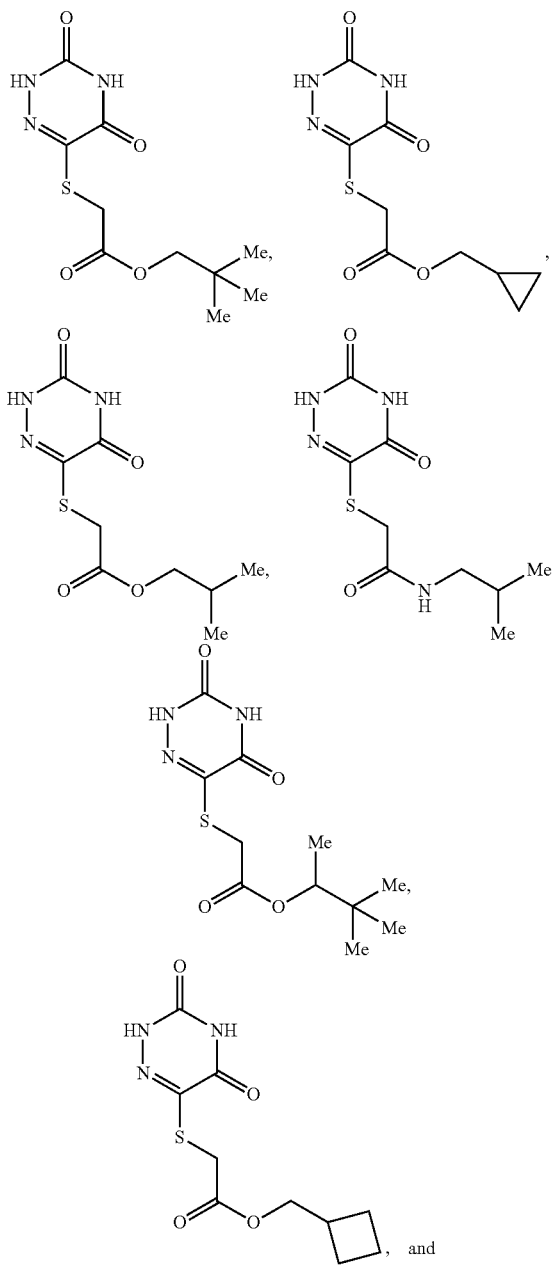

-continued

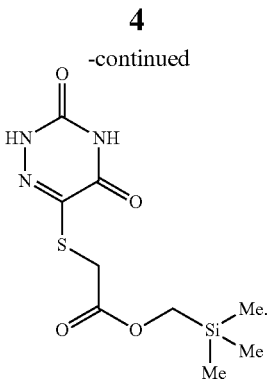

In yet another aspect, the invention is a method of inhibiting virulence in Gram-negative bacteria comprising contacting the bacteria with one or more of the inventive pyrrole compounds. In another embodiment of this method, the bacteria are pathogenic to marine life and the compound or compounds are administered to the marine life as a feed additive.

In another aspect, the invention is a bacterial biofilm-inhibiting composition comprising one or more of the inventive pyrrole compounds.

In another aspect, the invention is a method of controlling quorum sensing Gram-negative bacteria on a surface, comprising exposing the bacteria to one or more of the inventive pyrrole compounds, in an amount that affects biofilm formation. In one embodiment of this method, the surface is a solid.

In yet another aspect, the invention is a device that is coated or embedded with one or more of the inventive pyrrole compounds to prevent bacterial biofilm formation or bacterial transmission.

DETAILED DESCRIPTION OF THE INVENTION

Figure 1:
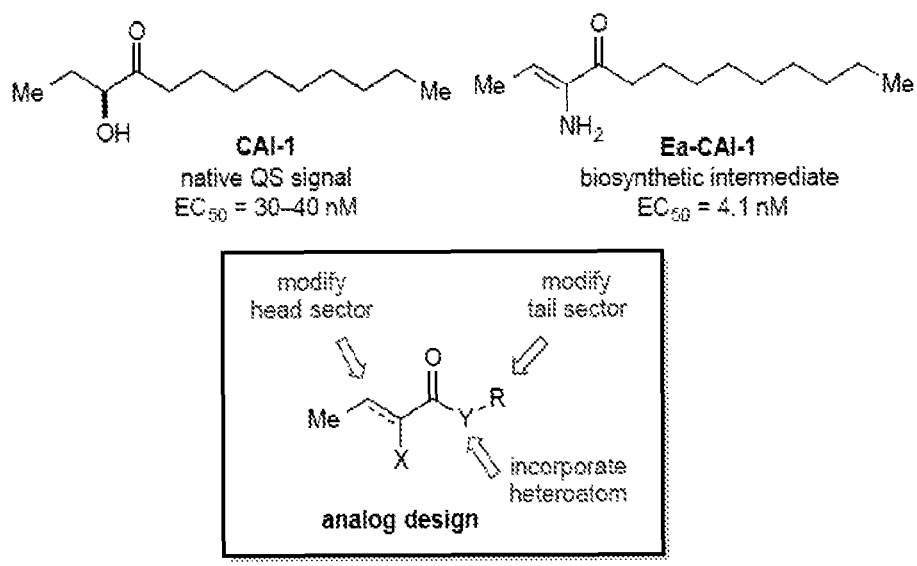
FIG. 1. Structure of CAI-1 and Ea-CAI-1 and design of agonist.

In *V. cholerae*, the native QS signal is CAI-1 ((S)-3-hydroxytridecan-4-one). Ea-CAI-1 is an intermediate in the CAI-1 biosynthetic pathway. Ea-CAI-1 is less chemically stable than CAI-1 but is an order of magnitude more potent as a QS agonist than the native, longer-lived CAI-1. With an aim to determine target structures that achieve higher potency and improved chemical stability over the native QS signal in *V. cholerae*, a series of analogs of Ea-CAI-1 were synthesized (FIG. 1).

Using rational molecule design principles based on a wealth of structure-activity relationships (SAR), a structurally distinct and potent series of synthetic small molecule modulators of quorum sensing were identified which cause repression of virulence factor expression and biofilm formation in pathogenic bacteria. The molecules may be employed to affect QS behaviors of *V. cholerae* or other pathogenic bacteria that utilize *V. cholerae*-type quorum sensing circuits such as *Legionella* species. (e.g., *L. pneumophila*) and *Vibrio* species. (e.g., *V. cholera, V. vulnificus, V. parahaemolyticus, V. alginolyticus, V. anguillarum, V. carchariae, V. damsel, V. ordalii*).

The general structure of compounds that were synthesized can be described as follows:

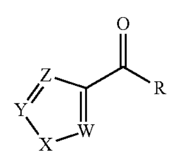

W=N, C
X=N, C, O
Y=N, C
Z=N, C
R=hydrocarbon chain which may contain alkyl, alkenyl, or aryl groups The series of agonists described herein were designed and assayed with the goal of identifying molecules that, like Ea-CAI-1, demonstrate high QS agonist activity and, in an improvement over Ea-CAI-1, possess the chemical stability of a useful probe or drug candidate. Compounds were synthesized and assayed for activity and are shown in Scheme 1 and Scheme 2 and also in FIGS. 2, 6, and 8.

Ea-CAI-1, a delicate biosynthetic intermediate and the most potent natural agonist of QS in *V. cholerae*, was used as a starting point in designing chemically stable analogs with high potency in activating the CqsS receptor. Several derivatives of the 3-acylpyrrole structure have activities equivalent to Ea-CAI-1 and are promising leads for developing new therapeutics to control *V. cholerae* infection, for example the 3-acylpyrrole with the C9 alkyl tail, compound 18.

The agonists that were synthesized ("pro-QS" molecules) induced *V. cholerae* cells to exhibit high cell density behaviors regardless of their actual cell density. Most notable of these behaviors is repression of genes encoding virulence factors and those required for biofilm formation. Numerous human pathogens from the *Vibrio* genus have been shown to operate under this system wherein QS represses virulence and biofilm traits at high cell density (e.g., *V. parahaemolyticus, V. alginolyticus*, and *V. vulnificus*).

Molecules that activate the QS system of *V. cholerae* are referred to as pro-QS agents, of which there are two varieties that are especially suited to therapeutic uses. The first is the set of small molecules identified herein which may be classified as QS receptor agonists. The second is a set of small molecules that have been previously identified and classified as LuxO inhibitors (PCT/US2013/026837) that function uncompetitively to perturb LuxO ATPase activity. The inhibitors broadly activate different *Vibrio* QS circuits and, in turn, repress virulence factor production and reduce cytotoxicity. The present invention encompasses combined administration of molecules from the first set of QS receptor agonists and the second set of LuxO inhibitors for the treatment of bacterial pathogenicity.

The invention encompasses use of LuxO inhibitors and QS receptor agonists to treat active infection and for prophylactic measures. Use of these molecules as prophylactics serves to prevent *V. cholerae* or other pathogenic vibrios from initiating the low cell density virulence gene expression program that is required for colonization. In this embodiment, inhibiting the launch of virulence factors would provide sufficient time for the host immune system to eliminate the pathogen. In contrast to traditional antibiotics that target essential bacterial processes, growth is not affected by interfering with QS, so development of bacterial resistance could potentially be minimized. Thus, just as antagonizing QS in bacteria is an alternative to traditional antibiotics, so is the use of pro-QS agents.

Some of the uses for the inventive molecules are herein described. In one embodiment, the invention provides a pharmaceutical composition comprising one or more compounds of the present invention or a pharmaceutically-acceptable salt thereof, and a pharmaceutically acceptable carrier, adjuvant or vehicle. Treatment comprises administering to the host of the bacteria a therapeutically effective amount of the pharmaceutical composition of this invention. A skilled artisan can determine which form of administration is best and the therapeutic amount for balancing the dose versus periodic delivery.

Infectious bacteria that use quorum sensing strategies to produce virulence include pathogens to humans, animals, and plants. Some pathogens infect marine life and thereafter cause disease in humans who eat or otherwise come into contact with the marine life. *Vibrio* species may contaminate shellfish and cause food poisoning. The methods described herein to inhibit bacterial infection include methods to inhibit bacterial infection of marine life such as by administering the inventive compounds as feed supplements or by applying the compounds to devices or cages to prevent growth of bacteria or formation of bacterial biofilms.

The following examples set forth the general procedures involved in practicing the present invention. To the extent that specific materials are mentioned, it is merely for purposes of illustration and is not intended to limit the invention.

EXPERIMENTAL

Ea-CAI-1 Analogs of Varying Tail Lengths

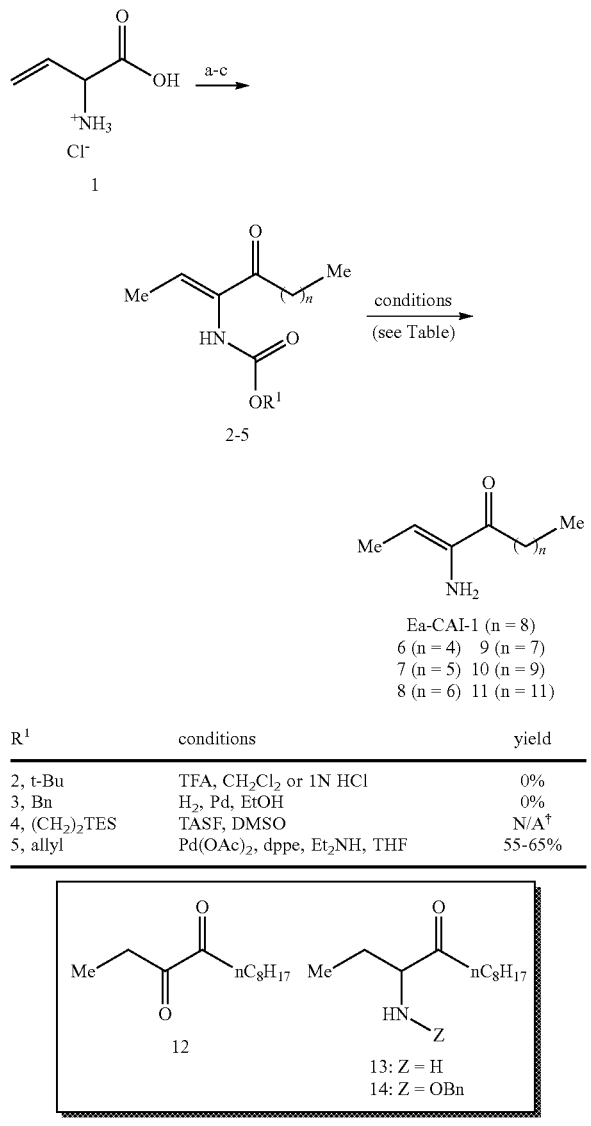

Scheme 1. Synthesis of Ea-CAI-1 and tail length-modified analogs.

| R¹ | conditions | yield |
|---|---|---|
| 2, t-Bu | TFA, CH$_2$Cl$_2$ or 1N HCl | 0% |
| 3, Bn | H$_2$, Pd, EtOH | 0% |
| 4, (CH$_2$)$_2$TES | TASF, DMSO | N/A[†] |
| 5, allyl | Pd(OAc)$_2$, dppe, Et$_2$NH, THF | 55-65% |

Reagents and conditions:
(a) Amine protection;
(b) HNMe(OMe)•HCl, EDC, HOBt, Et$_3$N, THF (42-58% from 1);
(c) R$^2$MgX (71-93%).
[†]These conditions led to quantitative consumption of the starting material and slow formation of the desired product along with inseparable silyl byproducts.

Synthesis of the Ea-CAI-1 analogs of varying tail lengths required development of an effective enamine protecting group strategy. Deprotection of the enamino ketone functionality (2-5) is significantly complicated by the high propensity of the product (Ea-CAI-1) to undergo hydrolysis to the α-diketone 12. As shown in Scheme 1, efforts to employ a t-Boc protecting group strategy (2, R$^1$=tBu) were unsuccessful; this functionality could not be removed under standard conditions. Similarly, attempts to reductively remove the Cbz group of 3 (R$^1$=Bn) through exposure to H$_2$ and Pd led to two major products, which were tentatively identified as aminoketone 13 and N-Cbz analog 14; these compounds presumably arise via preferential reduction of the alkene unit prior to benzyl cleavage. Although the N-Teoc protecting group (4) could be removed by treatment with excess TASF in DMSO, this transformation was very slow and yielded the desired adduct along with inseparable silyl-byproducts. The N-Alloc protecting group (5, R=allyl) was most effective; upon exposure to Pd(PPh$_3$)$_4$ and Et$_2$NH, 5 was rapidly deprotected to deliver Ea-CAI-1 in good yield. Importantly, the product was isolated in pure form after passage through a short plug of silica gel deactivated with Et$_3$N. Using this Alloc protecting group strategy, a series of tail-length modified Ea-CAI-1 analogs (6-11) was prepared.

The "tail-modified" analogs (6-11) were evaluated in a CqsS agonist bioassay (Table 1). The *V. cholerae* CqsS receptor was somewhat promiscuous with respect to variations in tail length. (This observation is consistent with similar evaluation of tail-length modified CAI-1 analogs). The parent compound (Ea-CAI-1, n=8) and the analog bearing a one-carbon truncated tail (9, n=7) show low nM activity and full activation (entries 4 and 5). Other analogs with shorter (6-8) or longer (10) tail lengths were 1-2 orders of magnitude less potent, but nonetheless promoted full activation (entries 1-3 and 6). Only a very long tail gave an analog (11, n=11) that was much less active, even at high concentrations. There was no observed direct correlation between maximum % response and EC$_{50}$. Small perturbations in the structure of the ligand or binding site can presumably disrupt the balance between kinase and phosphatase activity. In all cases, the Ea-CAI-1 analogs were more active by an order of magnitude compared to the related examples from a native CAI-1 series.

TABLE 1

Effect of Ea-CAI-1 tail length on QS agonist activity.

| Entry | | EC$_{50}$ (nM)[a] | % Response[b] |
|---|---|---|---|
| 1 | 6, n = 4 | 590 | 100 |
| 2 | 7, n = 5 | 290 | 120 |
| 3 | 8, n = 6 | 40 | 109 |
| 4 | 9, n = 7 | 2.6 | 112 |
| 5 | Ea-CAI-1, n = 8 | 4.1 | 100 |
| 6 | 10, n = 9 | 170 | 105 |
| 7 | 11, n = 11 | >225000 | 38 |

Values were determined using the CqsS agonist bioassay.
[a]All EC$_{50}$ values are the mean of triplicate analyses.
[b]Percent maximal bioluminescence with respect to Ea-CAI-1, which is set at 100%.

Ea-CAI-1 Analogs of Substitute Head Domain and Diverse Tail Structure

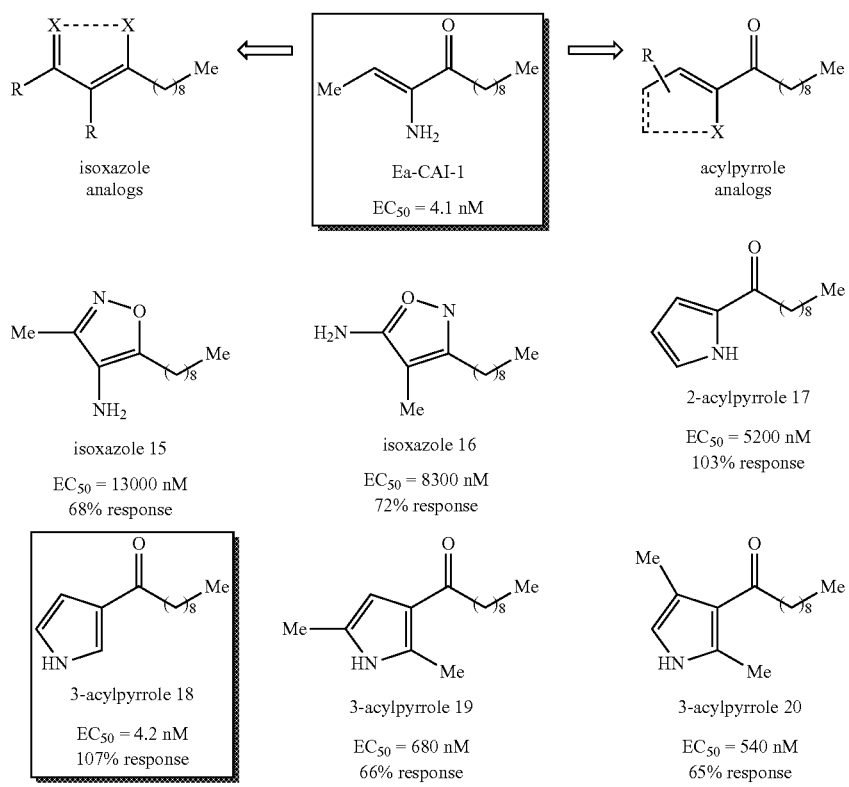

Scheme 2. Variation of the Ea-CAI-1 head group: isoxazole and acylpyrrole analogs.

Pyrrole Synthesis:

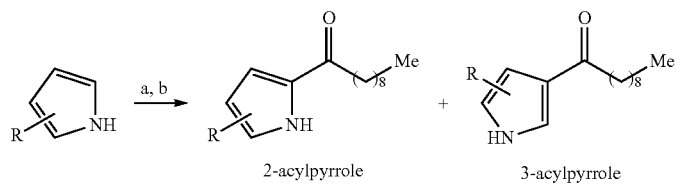

Reagents and conditions: (a) MeMgBr, Et$_2$O; (b) n-C$_9$H$_{19}$COCl.

The next set of Ea-CAI-1 analogs that were created can be generally described as having replaced the enamino ketone "head" domain with more stable functionality, and of having installed greater structural diversity onto the "tail" sector.

The effects of head group variation on agonist activity was examined first. Attempts to mimic the stereoelectronic features of the enamino ketone motif of the parent compound were made through substitution with more stable isoxazole or acylpyrrole functional motifs (Scheme 2). A series of analogs was synthesized and evaluated for agonist activity. Neither of the isoxazole analogs showed significant activity (15 and 16, EC$_{50}$>8000 nM). However, promising results were obtained with the series of analogs bearing acyl pyrrole head groups; importantly, these motifs retain both ketone and α-heteroatom hydrogen bond donor functionality. For the initial analysis, compounds 17 and 18 were prepared as a readily separable mixture of isomers for biological evaluation (Scheme 2). While both analogs elicit the full level of QS response, the 3-acyl isomer 18 exhibits an EC$_{50}$>1000-fold more potent than the 2-acyl isomer. The EC$_{50}$ value of 4.2 nM identifies 18 as comparable in activity to the parent compound, Ea-CAI-1. Incorporation of additional substituents onto the 3-acyl pyrrole (19 and 20) resulted in lower agonist activity, as indicated by the higher EC$_{50}$ and lower % response.

The 3-acylpyrrole heterocyclic motif has therefore been identified as a viable, chemically stable bioisostere of the native Ea-CAI-1 head group. The next set of analogs probed the effect of variations in the tail structure on CqsS agonist activity (Table 2). Analogs bearing a C9 or a C10 fatty acid tail were most potent and provided full activation (entries 4 and 5); these findings are comparable to the structure-activity relationships observed in the α-enamino ketone series. The other tail lengths were less potent and gave no more than 50% activation.

TABLE 2

Effect of 3-acylpyrrole tail length on QS agonist activity.

[Structure: 3-acylpyrrole with C(=O)-(CH2)$_m$-Me tail]

| Entry | | EC$_{50}$ (nM)$^a$ | % Response$^b$ |
|---|---|---|---|
| 1 | 21, n = 4 | 1200 | 14 |
| 2 | 22, n = 5 | 740 | 43 |
| 3 | 23, n = 6 | 51 | 50 |
| 4 | 24, n = 7 | 8.2 | 100 |
| 5 | 18, n = 8 | 4.2 | 110 |
| 6 | 25, n = 9 | 300 | 29 |

Values were determined using the CqsS agonist bioassay.
$^a$All EC$_{50}$ values are the mean of triplicate analyses.
$^b$Percent maximal bioluminescence with respect to Ea-CAI-1, which is set at 100%.

Figure 2:
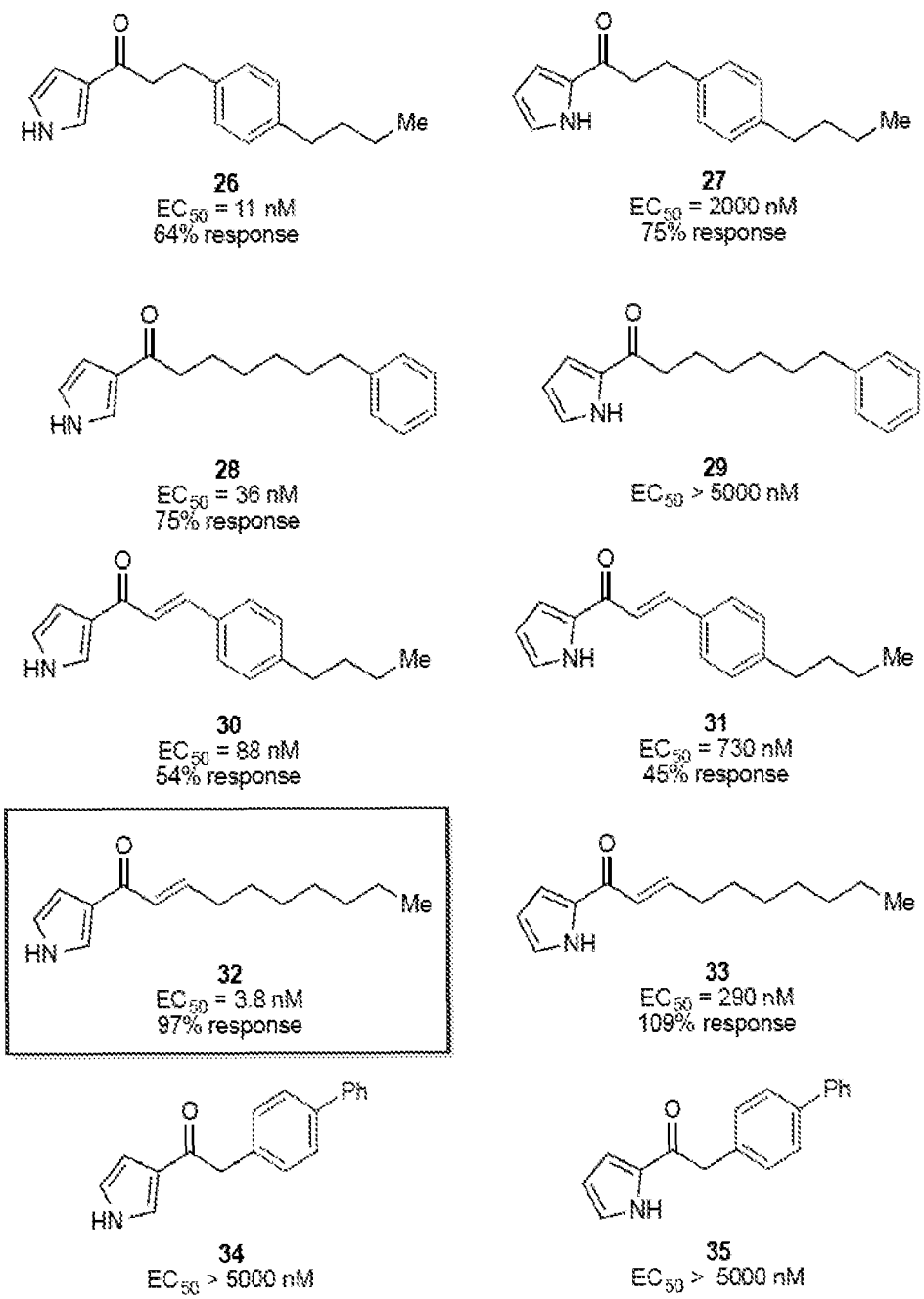
FIG. 2. Modified tail structures in the 2- and 3-acylpyrrole motif.

Further probing of the effect of tail structure involved introduction of simple E-alkene units and benzene rings, with the goal of examining the effects of conformational restriction and steric perturbation within the acyl tail (FIG. 2). In all cases in which significant activity was observed (EC$_{50}$ values<5000 nM), the 3-acyl pyrrole analogs were much more potent than the corresponding 2-acyl pyrrole analogs. Introduction of a benzene ring in the 3-acylpyrrole series produced highly active analogs; compounds 26 and 28 show activities only 3- to 10-fold lower than the best agonists (Ea-CAI-1 and acylpyrrole 18). This result suggests substantial steric flexibility in the presumed hydrophobic binding site for the tail group and expands the design opportunities for further exploration of the tail structure. However, the maximum percent activation is lower for these benzyl analogs (54-75%). In previous SAR work focused on the structure of the fatty acid tail of CAI-1, the conformational restriction provided by incorporation of an E-alkene unit conferred enhanced potency over the corresponding fully saturated analog. Similarly, in the 3-acylpyrrole Ea-CAI-1 series, incorporation of an E-alkene moiety (32) leads to the one of the most potent agonists of *V. cholerae* QS yet discovered; compound 32, with an EC$_{50}$ of 3.8 nM, is slightly more potent than both Ea-CAI-1 (4.1 nM) and acyl-pyrrole 18 (4.2 nM). Yet, incorporation of a biphenyl unit in the acyl chain leads to essentially inactive analogs (34 and 35).

Effect of Compound 18 on the QS Circuit

Figure 3:
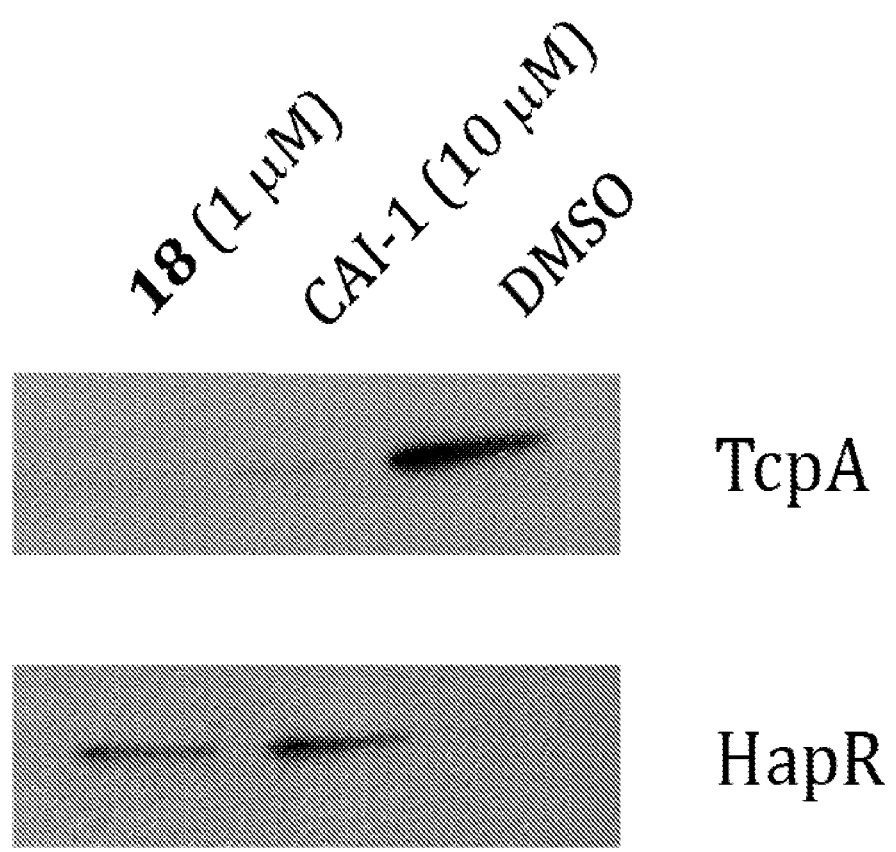
FIG. 3. CAI-1 and Compound 18 repress production of the *V. cholerae* toxin-correlated pilus TcpA and activate production of HapR. DMSO is used as control.

Having identified a stable and highly potent lead compound (18), examination proceeded on its effect on the QS circuit in *V. cholerae*. In vivo, HapR is a transcription factor that functions as one of two master QS regulators in *V. cholerae*. Agonism of CqsS leads to increased production of HapR and HapR, in turn, drives the high-cell density gene expression program, which leads to repression of the expression of genes required for virulence and biofilm formation. FIG. 3 shows that production of HapR increased in response to 1 μM of the 3-acyl pyrrole 18 to a level similar to that achieved from exposure to 10 μM of the native ligand, CAI-1. Conversely, production the major *V. cholerae* virulence factor, TcpA, (toxin-co-regulated pilis protein subunit A), is repressed by both CAI-1 and compound 18. These results are consistent with the heterocyclic analog 18 acting on CqsS in a manner similar to CAI-1.

Effect of Compound 18 on Cytotoxicity

Figure 4:
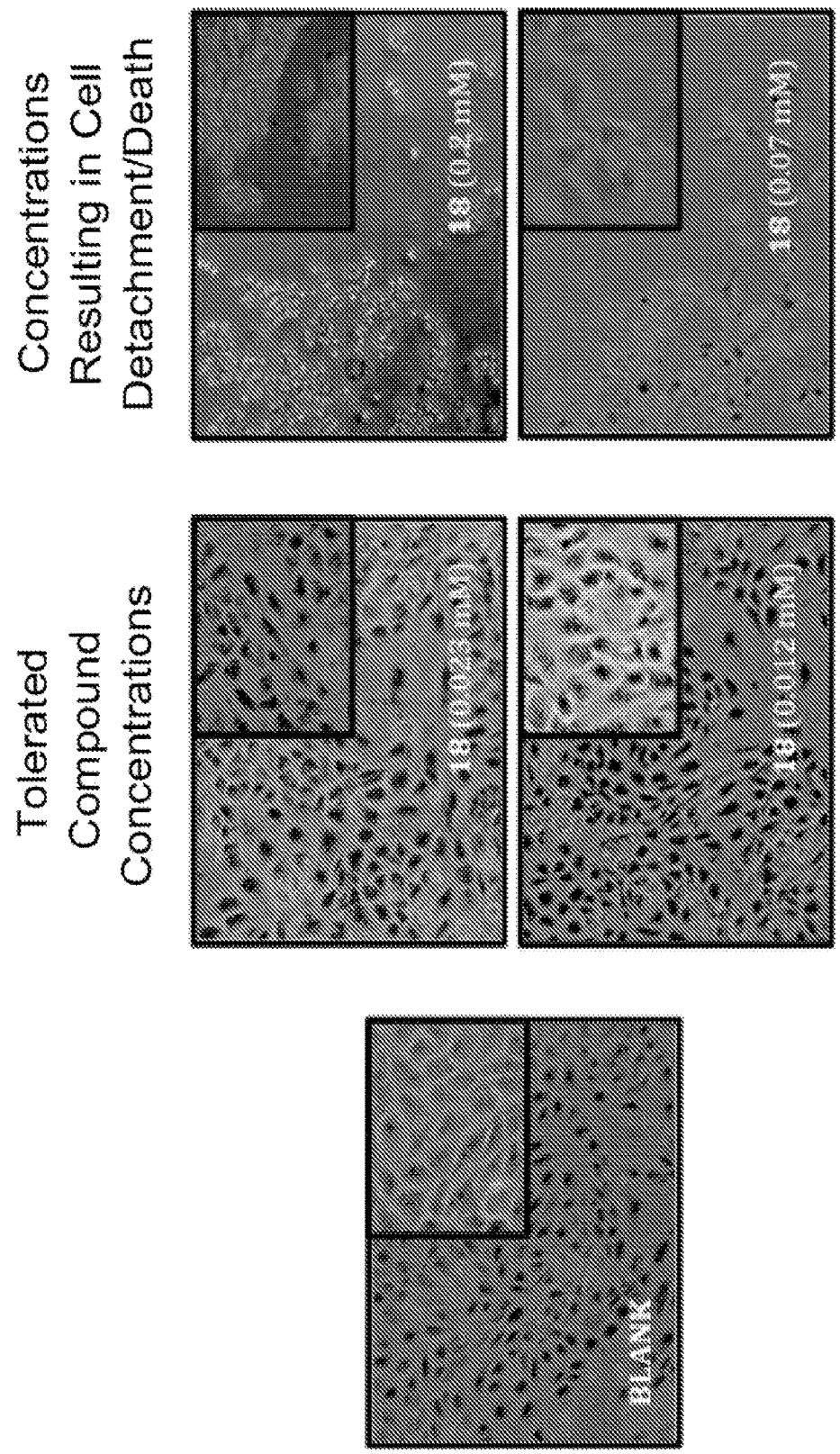
FIG. 4. Murine 3T3 fibroblast cell toxicity assay. Effects of different concentrations of Compound 18 on 3T3 cells.

Given the possibility for further development of the 3-acylpyrrole 18 as a potential anti-virulence agent, a preliminary investigation was made of the cytotoxicity of this analog in bacteria and in a murine 3D3 fibroblast cell line. Consistent with our proposal that the molecule functions by influencing QS-controlled behaviors and not by altering growth, compound 18 was not toxic to bacteria. No decrease in OD$_{600}$ occurred when *V. cholerae* was treated with 18 at concentrations up to 25,000 nM (i.e. levels more than 5000-fold higher than the EC$_{50}$ for 18). Likewise, 18 was tolerated by murine 3T3 fibroblast cells at concentrations up to 23,000 nM, as assessed by optical microscopy (FIG. 4). Compound 18 functions analogously to the native signal, CAI-1, in regulating production of the transcription factor HapR and the virulence factor, TcpA (FIG. 3). Compound 18 does not inhibit bacterial growth (FIG. 9) nor does it show toxicity toward a mamalian cell line (FIG. 4), and is therefore a promising candidate.

Effect of Compound 18 on *V. Harveyi*

Despite the high activity of this class of molecules with respect to the *V. cholerae* CqsS receptor, none of the 3-acyl pyrrole analogs showed significant activity against the *Vibrio harveyi* CqsS receptor. This result is perhaps surprising, given the high homology between these two QS receptors; however, it is consistent with earlier observations that, compared to the *V. cholerae* receptor, the *V. harveyi* receptor is less tolerant of structural perturbations to the cognate ligand.

Bioassay Data

*Vibrio cholerae* Agonism Bioassay

The molecules were bioassayed in a system that exploits the *V. cholerae* quorum sensing circuit. The bioassay used a bacterial reporter strain to measure the QS response. Values for percent of activation correspond to the level of bioluminescence produced in the bacterial reporter strain at saturating concentrations of molecule compared to the maximal levels produced in the presence of a native autoinducer molecule (Ea-CAI-1). In the activity assay, activation of quorum sensing, as reported by induction of bioluminescence, tracks with in vivo repression of virulence factor production and biofilm formation in *V. cholerae*. The EC$_{50}$ values correspond to the concentrations that are required to activate quorum sensing to its half-maximal level.

Reporter strain MM920 (*V. cholerae* ΔcqsA ΔluxQ carrying pBB1 cosmid, which contains the *V. harveyi* luxCD-ABE luciferase operon) was used to assay agonist activity of each synthetic compound. This strain was grown in LB medium containing 10 μg/mL tetracycline at 30° C. for >16 hours and diluted 20-fold with the same medium. Two μL of each synthetic compound dissolved in DMSO in various concentrations was added to 200 μL of the diluted reporter strain in triplicate in a 96-well plate. Bioluminescence and OD$_{600}$ were measured in a PerkinElmer EnVision Multilabel Reader following 4-hour incubation at 30° C. with shaking. DMSO was used as the negative control.

Example of Dose-Response Curves from Bioassay and Data Extracted

Figure 5:
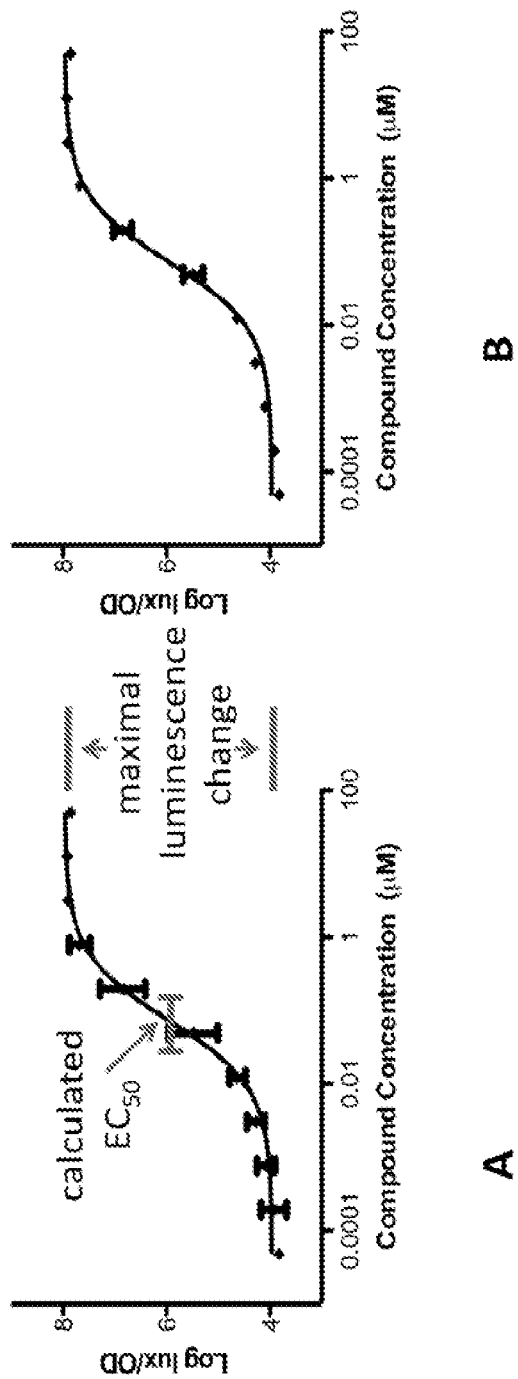
FIG. 5. Dose-response curves from bioassays. In 5A, the error bars represent the 95% confidence intervals; In 5B the standard deviation is shown.

FIG. 5 is an example of typical dose response curves highlighting the data that is represented in the Tables. Both of the dose-response curves were generated using GraphPad Prism 5 from the identical primary luminescence measurements.

The dose-response curve in FIG. 5A displays error bars that represent the 95% confidence intervals for each of the luminescence measurements. The curve in FIG. 5B displays the standard deviation of the data.

EC$_{50}$ values were calculated by Prism 5 using standard settings and are described in the Tables and text with the error representing the 95% confidence interval for the calculated EC$_{50}$ value.

The values for % response described in the Tables and text describe the maximal luminescence change for each of the analogs as a percent of EaCAI-1 or 18 (set at 100%). One of these molecules was included as a positive standard of activity for each of the assays. The error described within the tables represents the 95% confidence intervals for this data expressed as a percentage. While there is typically little variation in the maximal luminescence at saturation, there is some noise at low concentrations; compare for example the 95% confidence intervals for the points of low compound concentration and the points of high concentration on the left.

Complete Bioassay Data and 95% Confidence Intervals for all Compounds

Tabulated bioassay data for the compounds in Table 1

| Entry | Compound | Vibrio cholerae | |
|---|---|---|---|
| | | $EC_{50}$ (nM)[a] | % Response[b] |
| 1 | 6 (Me-CH=C(NH$_2$)-C(O)-(CH$_2$)$_4$-Me) | 594 ± 319 | 100 ± 57 |
| 2 | 7 (Me-CH=C(NH$_2$)-C(O)-(CH$_2$)$_5$-Me) | 286 ± 240 | 120 ± 117 |
| 3 | 8 (Me-CH=C(NH$_2$)-C(O)-(CH$_2$)$_6$-Me) | 40 ± 14.5 | 109 ± 25 |
| 4 | 9 (Me-CH=C(NH$_2$)-C(O)-(CH$_2$)$_7$-Me) | 2.6 ± 0.32 | 112 ± 7.0 |
| 5 | Ea-CAI-1 (Me-CH=C(NH$_2$)-C(O)-(CH$_2$)$_8$-Me) | 4.1 ± 0.45 | 100 ± 6.6 |
| 6 | 10 (Me-CH=C(NH$_2$)-C(O)-(CH$_2$)$_9$-Me) | 169 ± 32 | 105 ± 11 |
| 7 | 11 (Me-CH=C(NH$_2$)-C(O)-(CH$_2$)$_{10}$-Me) | >5000 | 38 |

[a] All $EC_{50}$ values are the mean of triplicate analyses.
[b] Percent maximal bioluminescence with respect to Ea-CAI-1, which is set at 100%.

Tabulated bioassay data for the compounds in Scheme 2 and FIG. 2.
| Entry | Compound | EC$_{50}$ (nM)[a] | % Response[b] |
|---|---|---|---|
| 1 |  15 | 13,090 ± 5,765 | 68 ± 52 |
| 2 |  16 | 8,263 ± 4,870 | 72 ± 56 |
| 3 |  17 | 5,166 ± 2,174 | 103 ± 91 |
| 4 |  18 | 4.2 ± 0.8 | 107 ± 10 |
| 6 | 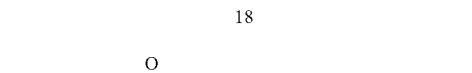 19 | 679 ± 92 | 66 ± 14 |
| 7 |  20 | 536 ± 80 | 65 ± 16 |
[a]All EC$_{50}$ values are the mean of triplicate analyses.
[b]Percent maximal bioluminescence with respect to Ea-CAI-1, which is set at 100%.
Tabulated bioassay data for the compounds in Table 2.
| Entry | Compound | EC$_{50}$ (nM)[a] | % Response[b] |
|---|---|---|---|
| 1 |  21 | 1152 ± 247 | 14 ± 50 |

| Entry | Compound | EC$_{50}$ (nM)$^a$ | % Response$^b$ |
|---|---|---|---|
| 2 | 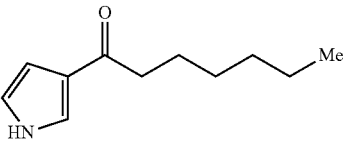 22 | 737 ± 472 | 43 ± 42 |
| 3 | 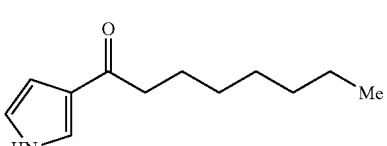 23 | 51 ± 15 | 50 ± 15 |
| 4 | 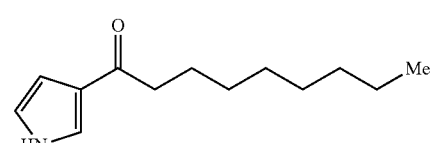 24 | 8.2 ± 2.0 | 101 ± 14 |
| 5 | 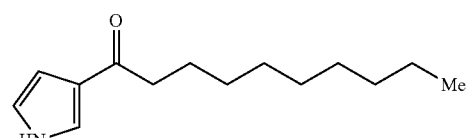 18 | 4.2 ± 0.8 | 107 ± 10 |
| 6 | 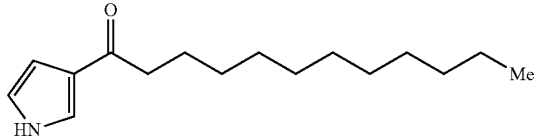 25 | 301 ± 98 | 29 ± 45 |
$^a$All EC$_{50}$ values are the mean of triplicate analyses.
$^b$Percent maximal bioluminescence with respect to Ea-CAI-1, which is set at 100%.
Tabulated bioassay data for the compounds in FIG. 3.
| Entry | Compound | EC$_{50}$ (nM)$^a$ | % Response$^b$ |
|---|---|---|---|
| 1 | 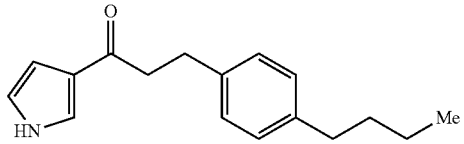 26 | 10.9 ± 4.8 | 64 ± 42 |
| 2 | 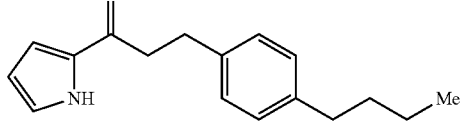 27 | 2017 ± 1681 | 75 ± 45 |

-continued
| Entry | Compound | EC$_{50}$ (nM)$^a$ | % Response$^b$ |
|---|---|---|---|
| 3 | 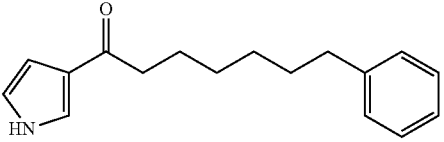 28 | 35.8 ± 6.1 | 75 ± 10 |
| 4 | 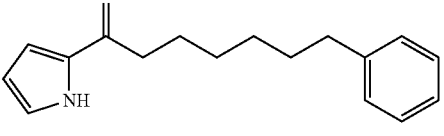 29 | >5000 | 60 |
| 5 | 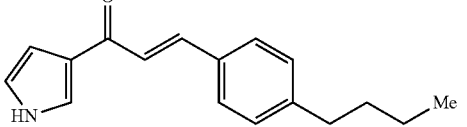 30 | 88.4 ± 24.9 | 54 ± 29 |
| 6 | 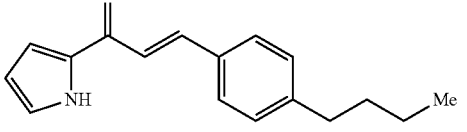 31 | 731 ± 686 | 45 ± 62 |
| 7 | 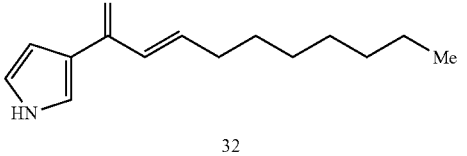 32 | 3.8 ± 0.4 | 97 ± 5 |
| 8 | 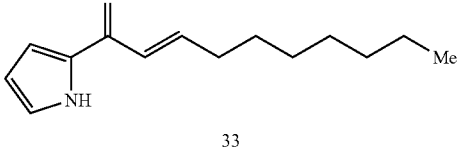 33 | 288 ± 92 | 109 ± 31 |
| 9 | 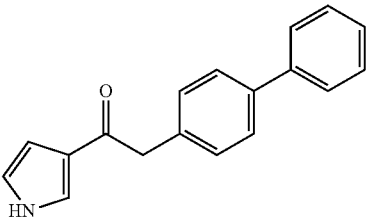 34 | >5000 | 25 |

| Entry | Compound | EC$_{50}$ (nM)[a] | % Response[b] |
|---|---|---|---|
| 10 | 35 | >5000 | 26 |

[a]All EC$_{50}$ values are the mean of triplicate analyses.
[b]Percent maximal bioluminescencewith respect to Ea-CAI-1, which is set at 100%.

General Structures and Additional Examples of Compounds

Figure 6:
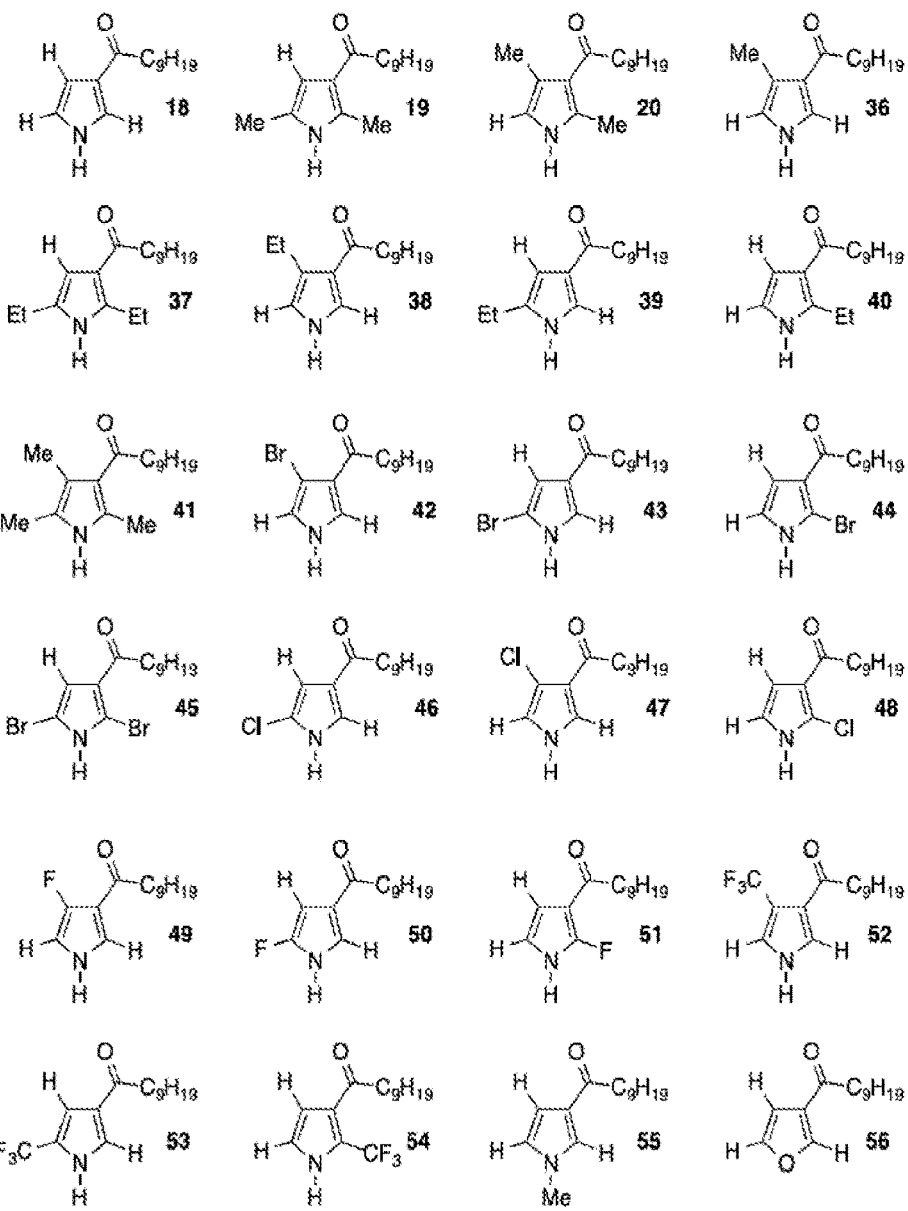
FIG. 6. Compounds that activate Quorum Sensing. A. General structural features of QS analog compounds. B. Examples of compounds.
Figure 7:
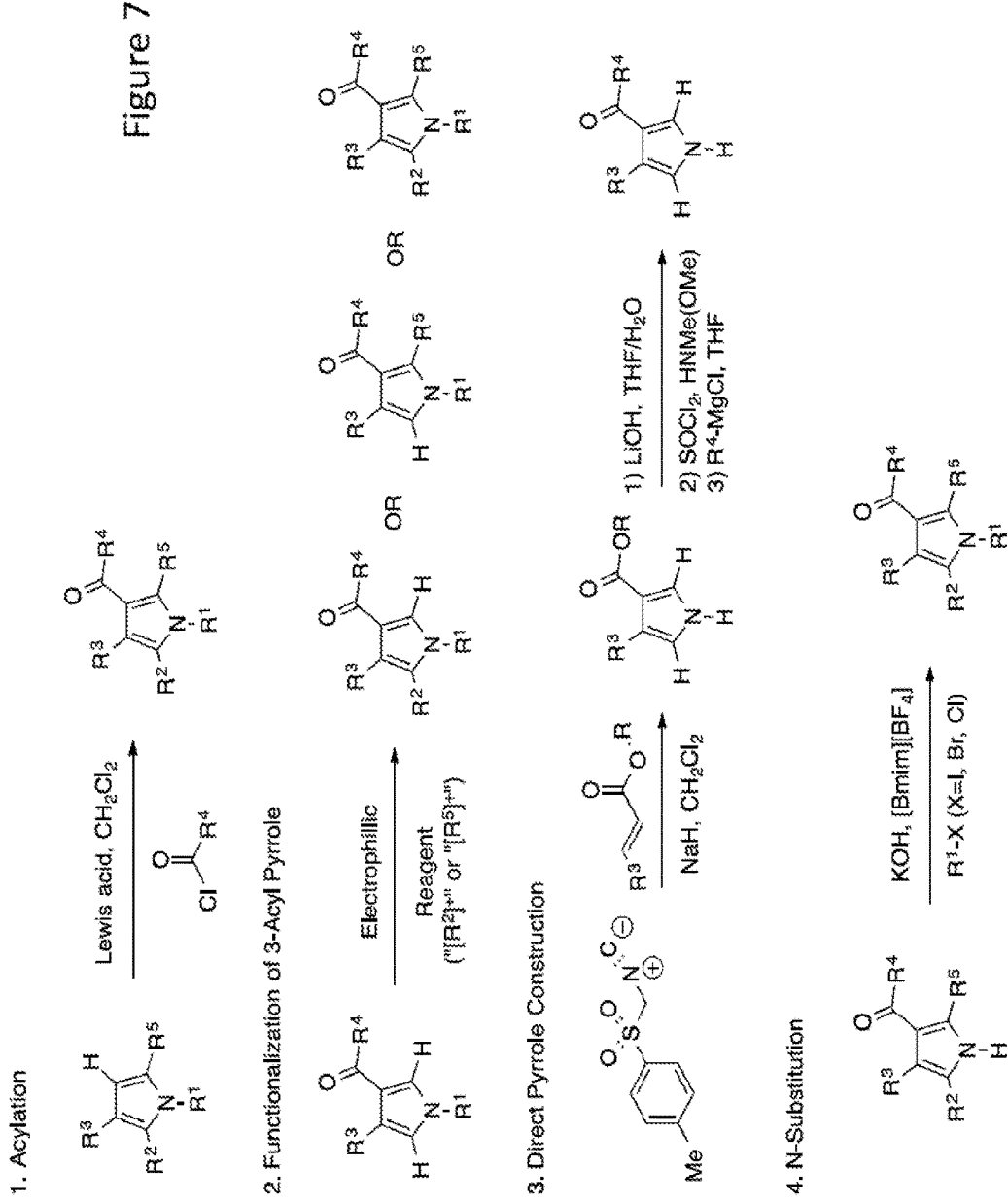
FIG. 7. Four general synthesis strategies for acyl pyrroles shown in FIG. 6.
Figure 8:
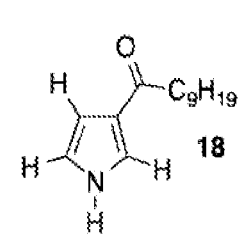
FIG. 8. Bioassay data for compounds tested for agonist activity. Superscript a indicates this is preliminary bioassay data for compounds 17, 18, 19 and 20. Superscript b indicates this value is at 50000 nM concentration.
Figure 8:
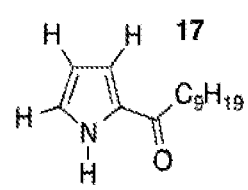
Figure 8:
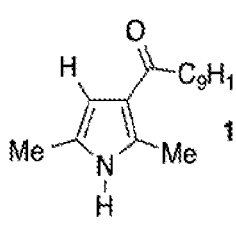
Figure 8:
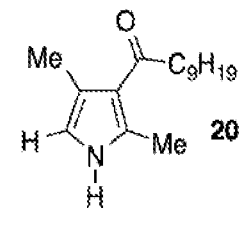
Figure 8:
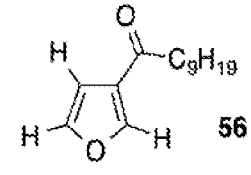
Figure 8:
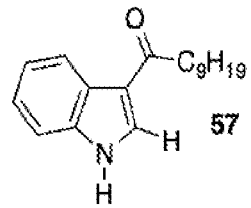

FIG. 6A provides the general structure of the synthetic compounds contemplated as QS agonists. FIG. 6B provides further examples of the synthetic compounds as well as the structures of compounds 18, 19, 20. FIG. 7 shows general synthesis strategies that were employed to synthesize 3-acyl pyrroles shown in FIG. 6. Bioassay data for some of the compounds is shown in FIG. 8.

Western Blot Analysis

Overnight cultures of *V. cholerae* CqsA-LuxQ— were diluted 1000-fold in AKI medium containing the indicated compounds. The cultures were grown under static conditions at 37° C. for 4 h and then were shaken for 18 h at 37° C. Cells were collected by centrifugation, TcpA and HapR from different samples were analyzed by Western Blot as described in references [4, 5].

Murine 3T3 Fibroblast Cell Toxicity Assay

3T3 cells were prepared in a 24-well plate and incubated for 24 h at 37° C. as described in NIH Publication No. 07-4518. Reference [6]. The culture media was replaced by media containing the compound 18 at the indicated concentrations and the plates were visually examined using a microscope for cytotoxicity after incubation in the presence of the compound for 24 h. FIG. 4 shows representative images displaying the effects of different concentrations of compound 18 on 3T3 cells.

Cytotoxicity of Compound 18 in *V. cholerae* as Assessed by OD$_{600}$

Figure 9:
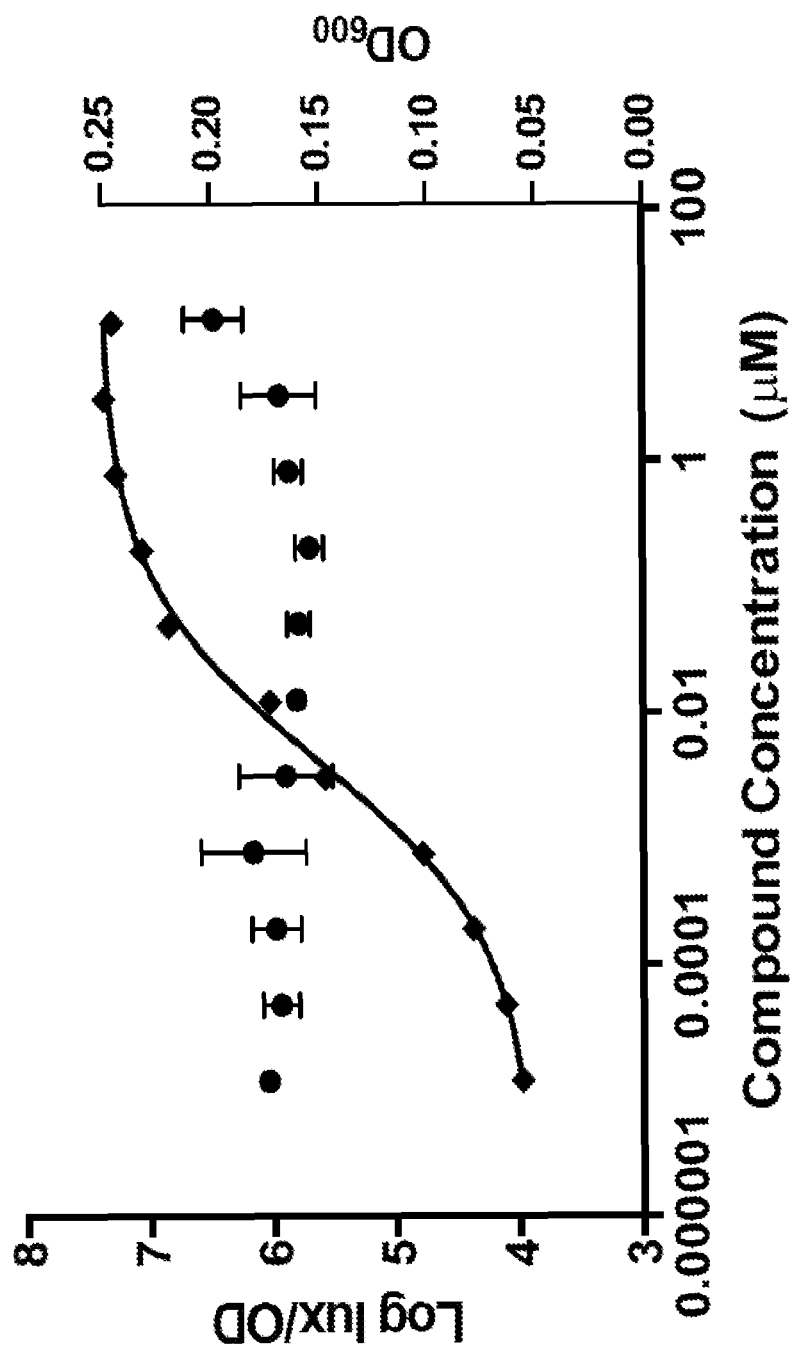
FIG. 9. Compound 18 has no effect on growth of *V. cholerae* strain MM920.

FIG. 9 is a plot showing the no effect on growth of *Vibrio cholerae* strain MM920 under the conditions described for biological assay. Diamonds represent luminescence measurements in the presence of varying concentrations of compound 18. Circles represent the OD$_{600}$ at each of the concentrations of 18.

General Experimental

Unless otherwise noted, all reactions were performed in flame-dried glassware under an atmosphere of nitrogen or argon using dried reagents and solvents. All chemicals were purchased from commercial vendors and used without further purification. Anhydrous solvents were purchased from commercial vendors.

Flash chromatography was performed using standard grade silica gel 60 230-400 mesh from SORBENT Technologies. Silica gel was loaded into glass columns as a slurry. Analytical thin-layer chromatography was carried out using Silica G TLC plates, 200 μm with UV$_{254}$ fluorescent indicator (SORBENT Technologies), and visualization was performed by staining and/or by absorbance of LTV light.

NMR spectra were recorded using a Bruker Avance II (500 MHz for $^1$H; 125 MHz for $^{13}$C) spectrometer fitted with either a $^1$H-optimized TCI (H/C/N) cryoprobe or a $^{13}$C-optimized dual C/H cryoprobe. Chemical shifts are reported in parts per million (ppm) and were calibrated according to residual protonated solvent. High-resolution mass spectral analysis was performed using an Agilent 1200-series electrospray ionization—time-of-flight (ESI-TOF) mass spectrometer in the positive ESI mode.

Compound Synthesis (Z)-benzyl (1-(methoxy(methyl)amino)-1-oxobut-2-en-2-yl)carbamate, 3a. To a solution of (Z)-2-(benzyloxycarbonylamino)but-2-enoic acid[1] (800 mg, 3.4 mmol) in DMF (16.7 mL) at ambient temperature and was treated with HOBt (1.2 g, 9.17 mmol), HNMe(OMe)-HCl (814 mg, 8.3 mmol), EDC (2.4 g, 12.5 mmol), and Et$_3$N (2.3 mL, 16.7 mmol) sequentially and the mixture was allowed to stir for 10 h at ambient temperature. The crude mixture was filtered through a plug of celite and concentrated in vacuo. The resulting oil was purified by silica gel chromatography eluting with a gradient from hexanes to 60% EtOAc/hexanes. Fractions containing the desired product were combined and concentrated in vacuo to provide (Z)-benzyl (1-(methoxy(methyl)amino)-1-oxobut-2-en-2-yl)carbamate (100 mg, 11%). $^1$H-NMR (500 MHz, CDCl$_3$) δ 7.39-7.21 (m, 5H); 6.99 (s, 1H); 5.69 (bs, 1H); 5.05 (s, 2H); 3.62 (s, 3H); 3.22 (s, 3H); 1.66 (d, J=7.1 Hz, 3H). $^{13}$C-NMR (125 MHz, CDCl$_3$) δ 167.1, 153.7, 135.9, 128.5, 128.2, 128.2, 128.1, 121.7, 67.1, 60.8, 34.6, 12.5. HRMS (ESI-TOF) 279.1351 [M+H]$^+$ (calculated for C$_{14}$H$_{19}$N$_2$O$_4$=279.1345).

(Z)-benzyl (4-oxotridec-2-en-3-yl)carbamate, 3. To a solution of (Z)-benzyl (1-(methoxy(methyl)amino)-1-oxobut-2-en-2-yl)carbamate (100 mg, 0.359 mmol) in THF (3.6 mL) at 0° C. was added nonyl-MgBr (1.0M in Et$_2$O, 1.8 mL, 1.8 mmol) and the mixture was stirred at 0° C. for 5 h. The reaction was quenched with sat. NH$_4$Cl, extracted with Et$_2$O (3×10 mL), the combined organics were washed with brine, dried over Na$_2$SO$_4$ and concentrated in vacuo. The residue was purified by silica gel chromatography eluting with 10% EtOAc/hexanes to 40% EtOAc/hexanes to provide (Z)-benzyl (4-oxotridec-2-en-3-yl)carbamate (72 mg, 58%) $^1$H-NMR (500 MHz, CDCl$_3$) δ 7.45-7.29 (m, 5H); 6.66 (s, 1H); 6.57 (q, J=7.1 Hz, 1H); 5.11 (s, 2H); 2.64 (t, J=7.5 Hz, 2H); 1.86 (d, J=7.1 Hz, 3H); 1.56-1.51 (m, 2H); 1.37-1.14 (m, 12H); 0.85 (t, J=6.9 Hz, 3H). $^{13}$C-NMR (125 MHz, CDCl$_3$) δ197.7, 153.9, 136.2, 134.9, 131.4, 128.8, 128.5, 128.4, 67.5, 36.8, 31.9, 29.9, 29.4, 29.3, 25.8, 24.8, 22.8, 15.4, 14.3. HRMS (ESI-TOF) 346.2388 [M+H]$^+$ (calculated for C$_{21}$H$_{32}$NO$_3$=346.2382).

(Z)-2-(trimethylsilyl)ethyl (1-(methoxy(methyl)amino)-1-oxobut-2-en-2-yl)carbamate, 4a. L-Vinylglycine hydrochloride[1] (320 mg, 2.33 mmol) was dissolved in dioxane/H$_2$O (26 mL, 0.017M, 1:1 dioxane:H$_2$O) and was treated with NaHCO$_3$ (391 mg, 4.66 mmol) and N-[2-(Trimethylsilyl)ethoxycarbonyloxy]succinimide (633 mg, 2.44 mmol) sequentially at room temperature. The resulting mixture was stirred at room temperature for 24 h and was then concentrated in vacuo to a volume of ca. 10 mL. The resulting solution was acidified with 10% KHSO$_4$ to ~pH6.5, was extracted with DCM (3×50 mL), dried over Na$_2$SO$_4$ and concentrated to dryness. The resulting oil was dissolved in THF (23 mL) at ambient temperature and was treated with HOBt (944 mg, 6.99 mmol, 3.0 eq to VGly-HCl), HNMe(OMe)-HCl (341 mg, 3.5 mmol, 1.15 eq to VGly-HCl), EDC (671 mg, 3.5 mmol, 1.15 eq to VGly-HCl), and Et$_3$N (975 μL, 6.99 mmol, 3.0 eq to VGly-HCl) sequentially and the mixture was allowed to stir for 10 h at ambient temperature. The crude mixture was filtered through a plug of celite and concentrated in vacuo. The resulting oil was purified by silica gel chromatography eluting with a gradient from hexanes to 60% EtOAc/hexanes. Fractions containing the desired product were combined and concentrated in vacuo to provide (Z)-2-(trimethylsilyl)ethyl (1-(methoxy(methyl)amino)-1-oxobut-2-en-2-yl)carbamate as a pale yellow oil (280 mg, 42% from VGly-HCl). $^1$H-NMR (500 MHz, CDCl$_3$) δ 6.28 (s, 1H); 5.81-5.68 (m, 1H); 4.19-4.10 (m, 2H); 3.67 (s, 3H); 3.24 (s, 3H); 1.70 (d, J=7.0 Hz, 3H); 1.03-0.91 (m, 2H); −0.01 (s, 9H). $^{13}$C-NMR (125 MHz, CDCl$_3$) δ 167.2, 154.2, 130.1, 121.2, 64.1, 61.1, 34.3, 17.8, 12.6, −1.34. HRMS (ESI-TOF) 289.1578 [M+H]$^+$ (calculated for C$_{12}$H$_{25}$N$_2$O$_4$Si=289.1584).

(Z)-2-(trimethylsilyl)ethyl (4-oxotridec-2-en-3-yl)carbamate, 4. To a solution of (Z)-2-(trimethylsilyl)ethyl (1-(methoxy(methyl)amino)-1-oxobut-2-en-2-yl)carbamate (115.3 mg, 0.40 mmol) in THF (4 mL) at 0° C. was added nonyl-MgBr (1.0M in Et$_2$O, 2 mL, 2 mmol) and the mixture was stirred at 0° C. for 2 h. The reaction was quenched with 10% KHSO$_4$, extracted with Et$_2$O (3×10 mL), the combined organics were washed with brine, dried over Na$_2$SO$_4$ and concentrated in vacuo. The residue was purified by silica gel chromatography eluting with 10% EtOAc/hexanes to 40% EtOAc/hexanes to provide (Z)-2-(trimethylsilyl)ethyl (4-oxotridec-2-en-3-yl)carbamate (132.1 mg, 93%) $^1$H-NMR (500 MHz, CDCl$_3$) δ 6.55 (q, J=7.1 Hz, 1H); 6.53 (s, 1H); 4.19-4.12 (m, 2H); 2.64 (t, J=7.5 Hz, 2H); 1.86 (d, J=7.1 Hz, 3H); 1.64-1.51 (m, 2H); 1.33-1.17 (m, 12H); 0.94-0.86 (m, 2H); 0.85 (t, J=7.0 Hz, 3H); 0.01 (s, 9H). $^{13}$C-NMR (125 MHz, CDCl$_3$) δ 197.8, 154.3, 135.1, 131.2, 64.0, 36.8, 32.1, 29.6, 29.6, 29.5, 29.5, 24.8, 22.9, 17.8, 15.3, 14.3, −1.3. HRMS (ESI-TOF) 356.2623 [M+H]$^+$ (calculated for C$_{19}$H$_{38}$NO$_3$Si=356.2621).

(Z)-allyl (1-(methoxy(methyl)amino)-1-oxobut-2-en-2-yl)carbamate, 5a. To a solution of VGly-HC[1] (284.9 mg, 2.07 mmol) was dissolved in dioxane/H$_2$O (20 mL, 0.02M, 1:1 dioxane:H$_2$O) and was treated with NaHCO$_3$ (348 mg, 4.14 mmol) and allyl chloroformate (240 μL, 2.28 mmol) sequentially at room temperature. The resulting mixture was stirred at room temperature for 24 h and was then concentrated in vacuo to a volume of ca. 10 mL. The resulting solution was acidified with 10% KHSO$_4$ to ~pH6.5, was extracted with DCM (3×50 mL), dried over Na$_2$SO$_4$ and concentrated to dryness. The resulting oil was dissolved in THF (20.7 mL) at ambient temperature and was treated with HOBt (839 mg, 6.21 mmol), HNMe(OMe)-HCl (232 mg, 2.38 mmol), EDC (456 mg, 2.38 mmol), and Et$_3$N (1.4 mL, 10.35 mmol) sequentially and the mixture was allowed to stir overnight at ambient temperature. The crude mixture was filtered through a plug of celite and concentrated in vacuo. The resulting oil was purified by silica gel chromatography eluting with a gradient from hexanes to 60% EtOAc/hexanes. Fractions containing the desired product were combined and concentrated in vacuo to provide (Z)-allyl (1-(methoxy(methyl)amino)-1-oxobut-2-en-2-yl)carbamate as a pale yellow oil (200 mg, 42% from VGly-HCl). $^1$H-NMR (500 MHz, CDCl$_3$) δ 6.29 (s, 1H); 5.97-5.78 (m, 2H); 5.31 (d, J=17.3 Hz, 1H); 5.22 (d, J=10.4 Hz, 1H); 4.58 (d, J=5.7 Hz, 2H); 3.67 (s, 3H); 3.25 (s, 3H); 1.73 (d, J=7.1 Hz, 3H). $^{13}$C-NMR (125 MHz, CDCl$_3$) δ 167.1, 153.8, 132.5, 128.1, 118.5, 118.1, 61.2, 60.6, 34.2, 14.4. HRMS (ESI-TOF) 229.1192 [M+H]+(calculated for C$_{10}$H$_{17}$N$_2$O$_4$=229.1188).

(Z)-allyl (4-oxotridec-2-en-3-yl)carbamate, 5. To a solution of (Z)-allyl (1-(methoxy(methyl)amino)-1-oxobut-2-en-2-yl)carbamate (91.3 mg, 0.40 mmol) in THF (4 mL) at 0° C. was added nonyl-MgBr (1.0M in Et$_2$O, 2 mL, 2 mmol) and the mixture was stirred at 0° C. for 2 h. The reaction was quenched with 10% KHSO$_4$, extracted with Et$_2$O (3×10 mL), the combined organics were washed with brine, dried over Na$_2$SO$_4$ and concentrated in vacuo. The residue was purified by silica gel chromatography eluting with 10% EtOAc/hexanes to 40% EtOAc/hexanes to provide (Z)-allyl (4-oxotridec-2-en-3-yl)carbamate (98.3 mg, 83%) $^1$H-NMR (500 MHz, CDCl$_3$) δ 6.63 (s, 1H); 6.57 (q, J=7.1 Hz, 1H); 5.96-5.84 (m, 1H); 5.31 (dd, J=17.2, 1.4 Hz, 1H); 5.21 (dd, J=10.5, 1.3 Hz, 1H); 4.57 (d, J=5.6 Hz, 2H); 2.64 (t, J=7.6 Hz, 2H); 1.86 (d, J=7.1 Hz, 3H); 1.65-1.51 (m, 2H); 1.35-1.15 (m, 12H); 0.85 (t, J=7.0 Hz, 3H). $^{13}$C-NMR (125 MHz, CDCl$_3$) δ 197.7, 153.7, 134.9, 132.6, 131.4, 118.2, 66.3, 36.8, 32.1, 29.6, 29.6, 29.5, 29.5, 24.8, 22.9, 15.3, 14.3. HRMS (ESI-TOF) 296.2230 [M+H]$^+$ (calculated for C$_{17}$H$_{30}$NO$_3$=296.2226).

(Z)-allyl (4-oxonon-2-en-3-yl)carbamate, 6a. Prepared in a manner analogous to (Z)-allyl (4-oxotridec-2-en-3-yl)carbamate (5) from (Z)-allyl (1-(methoxy(methyl)amino)-1-oxobut-2-en-2-yl)carbamate and pentyl-MgBr to provide (Z)-allyl(4-oxonon-2-en-3-yl)carbamate (21.1 mg, 67%). $^1$H-NMR (500 MHz, CDCl$_3$) δ 6.62 (s, 1H); 6.57 (q, J=7.1 Hz, 1H); 5.98-5.81 (m, 1H); 5.31 (d, J=17.2 Hz, 1H); 5.21 (d, J=11.6 Hz, 1H); 4.57 (d, J=5.6 Hz, 2H); 2.65 (t, J=7.51 Hz, 2H); 1.86 (d, J=7.1 Hz, 3H); 1.68-1.51 (m, 2H); 1.34-1.15 (m, 4H); 0.86 (t, J=6.9 Hz, 3H). $^{13}$C-NMR (125 MHz, CDCl$_3$) δ 197.7, 153.8, 134.9, 132.6, 131.5, 118.3, 66.3, 36.7, 31.7, 24.5, 22.7, 15.3, 14.2. HRMS (ESI-TOF) 240.1602 [M+H]$^+$ (calculated for C$_{13}$H$_{22}$NO$_3$=240.1600).

(Z)-allyl (4-oxodec-2-en-3-yl)carbamate, 7a. Prepared in a manner analogous to (Z)-allyl (4-oxotridec-2-en-3-yl)carbamate (5) from (Z)-allyl (1-(methoxy(methyl)amino)-1-oxobut-2-en-2-yl)carbamate and hexyl-MgBr to provide (Z)-allyl (4-oxodec-2-en-3-yl)carbamate (27 mg, 81%). $^1$H-NMR (500 MHz, CDCl$_3$) δ 6.63 (s, 1H); 6.56 (q, J=7.1 Hz, 1H); 5.96-5.83 (m, 1H); 5.30 (d, J=17.2 Hz, 1H); 5.21 (d, J=11.6 Hz, 1H); 4.56 (d, J=5.6 Hz, 2H); 2.64 (t, J=7.6 Hz, 2H); 1.85 (d, J=7.1 Hz, 3H); 1.64-1.48 (m, 2H); 1.35-1.16 (m, 6H); 0.85 (t, J=6.9 Hz, 3H). $^{13}$C-NMR (125 MHz, CDCl$_3$) δ 197.4, 153.9, 134.8, 132.6, 131.5, 118.3, 66.2, 36.8, 32.0, 29.3, 24.8, 22.8, 15.4, 14.3. HRMS (ESI-TOF) 254.1756 [M+H]$^+$ (calculated for C$_{14}$H$_{24}$NO$_3$=254.1756).

(Z)-allyl (4-oxoundec-2-en-3-yl)carbamate, 8a. Prepared in a manner analogous to (Z)-allyl (4-oxotridec-2-en-3-yl)carbamate (5) from (Z)-allyl (1-(methoxy(methyl)amino)-1-oxobut-2-en-2-yl)carbamate and heptyl-MgBr to provide (Z)-allyl(4-oxoundec-2-en-3-yl)carbamate (26.6 mg, 76%). $^1$H-NMR (500 MHz, CDCl$_3$) δ 6.64 (s, 1H); 6.56 (q, J=7.1

Hz, 1H); 5.96-5.83 (m, 1H); 5.30 (d, J=18.2 Hz, 1H); 5.20 (d, J=10.4 Hz, 1H); 4.56 (d, J=5.6 Hz, 2H); 2.64 (t, J=7.5 Hz, 2H); 1.85 (d, J=7.5 Hz, 3H); 1.63-1.48 (m, 2H); 1.36-1.15 (m, 8H); 0.84 (t, J=6.8 Hz, 3H). $^{13}$C-NMR (125 MHz, CDCl$_3$) δ 197.1, 153.8, 134.9, 132.6, 131.5, 118.3, 66.3, 36.8, 31.9, 29.5, 29.3, 24.8, 22.8, 15.4, 14.3. HRMS (ESI-TOF) 268.1913 [M+H]$^+$ (calculated for $C_{15}H_{26}NO_3$=268.1913).

(Z)-allyl (4-oxododec-2-en-3-yl)carbamate, 9a. Prepared in a manner analogous to (Z)-allyl (4-oxotridec-2-en-3-yl) carbamate (5) from (Z)-allyl (1-(methoxy(methyl)amino)-1-oxobut-2-en-2-yl)carbamate and octyl-MgBr to provide (Z)-allyl(4-oxododec-2-en-3-yl)carbamate (27.9 mg, 78%). $^1$H-NMR (500 MHz, CDCl$_3$) δ 6.64 (s, 1H); 6.57 (q, J=7.1 Hz, 1H); 5.96-5.85 (m, 1H); 5.31 (d, J=17.2 Hz, 1H); 5.21 (d, J=10.4 Hz, 1H); 4.57 (d, J=5.6 Hz, 2H); 2.65 (t, J=7.5 Hz, 2H); 1.86 (d, J=7.1 Hz, 3H); 1.60-1.48 (m, 2H); 1.38-1.18 (m, 10H); 0.85 (t, J=6.8 Hz, 3H). $^{13}$C-NMR (125 MHz, CDCl$_3$) δ 197.7, 153.8, 134.9, 132.6, 131.5, 118.3, 63.3, 32.9, 32.0, 29.6, 29.5, 25.9, 24.8, 22.9, 15.4, 14.3. HRMS (ESI-TOF) 282.2065 [M+H]$^+$ (calculated for $C_{16}H_{28}NO_3$=282.2069).

(Z)-allyl (4-oxotetradec-2-en-3-yl)carbamate, 10a. Prepared in a manner analogous to (Z)-allyl (4-oxotridec-2-en-3-yl)carbamate (5) from (Z)-allyl (1-(methoxy(methyl) amino)-1-oxobut-2-en-2-yl)carbamate and decyl-MgBr to provide (Z)-allyl (4-oxotetradec-2-en-3-yl)carbamate (12.9 mg, 32%). $^1$H-NMR (500 MHz, CDCl$_3$) δ 6.64 (s, 1H); 6.57 (q, J=7.1 Hz, 1H); 5.97-5.84 (m, 1H); 5.31 (dd, J=17.2, 1.4 Hz, 1H); 5.21 (dd, J=10.4, 1.2 Hz, 1H); 4.57 (d, J=5.6 Hz, 2H); 2.65 (t, J=7.5 Hz, 2H); 1.86 (d, J=7.1 Hz, 3H); 1.66-1.50 (m, 2H); 1.37-1.16 (m, 14H); 0.85 (t, J=6.9 Hz, 3H). $^{13}$C-NMR (125 MHz, CDCl$_3$) δ 197.7, 153.8, 134.9, 132.6, 131.5, 118.2, 63.3, 37.6, 32.9, 32.1, 29.8, 29.8, 29.6, 29.5, 25.9, 22.9, 15.3, 14.3. HRMS (ESI-TOF) 310.2378 [M+H]$^+$ (calculated for $C_{18}H_{32}NO_3$=310.2382).

(Z)-allyl (4-oxohexadec-2-en-3-yl)carbamate, 11a. Prepared in a manner analogous to (Z)-allyl (4-oxotridec-2-en-3-yl)carbamate (5) from (Z)-allyl (1-(methoxy(methyl) amino)-1-oxobut-2-en-2-yl)carbamate and dodecyl-MgBr to provide (Z)-allyl (4-oxohexadec-2-en-3-yl)carbamate (28.9 mg, 65%). $^1$H-NMR (500 MHz, CDCl$_3$) δ 6.63 (s, 1H); 6.57 (q, J=7.1 Hz, 1H); 5.97-5.85 (m, 1H); 5.31 (d, J=17.2 Hz, 1H); 5.21 (d, J=10.4 Hz, 1H); 4.57 (d, J=5.6 Hz, 2H); 2.65 (t, J=7.5 Hz, 2H); 1.86 (d, J=7.1 Hz, 3H); 1.66-1.51 (m, 2H); 1.36-1.15 (m, 18H); 0.85 (t, J=6.9 Hz, 3H). $^{13}$C-NMR (125 MHz, CDCl$_3$) δ 197.7, 153.8, 134.9, 132.6, 131.4, 118.2, 63.3, 36.8, 33.0, 32.1, 29.9, 29.9, 29.8, 29.8, 29.6, 29.6, 24.8, 22.9, 15.4, 14.3. HRMS (ESI-TOF) 338.2696 [M+H]$^+$ (calculated for $C_{20}H_{36}NO_3$=338.2695).

(Z)-3-aminotridec-2-en-4-one, Ea-CAI-1. To a solution of (Z)-allyl (4-oxotridec-2-en-3-yl)carbamate (5) (8.6 mg, 0.029 mmol) in THF (300 µL) was added Et$_2$NH (45 µL, 0.435 mmol) followed by Pd(PPh$_3$)$_4$ (5.1 mg, 0.0044 mmol) and the mixture was allowed to stir at room temperature for 4 h in a flask shielded from light. The mixture was diluted with heptane (~1.5 mL) and concentrated to remove the THF. The remaining solution (~1 mL) was loaded onto a short plug of SiO$_2$ pre-equilibrated in hexane containing 1% Et$_3$N. The product was eluted with one column volume of hexane (1% Et$_3$N), 2 column volumes of 4:1 hexane:CH$_2$Cl$_2$ (1% Et$_3$N), 2 column volumes of 1:1 hexane:CH$_2$Cl$_2$ (1% Et$_3$N), 2 column volumes of 1:4 hexane:CH$_2$Cl$_2$ (1% Et$_3$N) and 1 column volume of CH$_2$Cl$_2$ (1% Et$_3$N). Fractions containing the desired product (R$_f$~0.4, 20% EtOAc/hexane, CAM stain) were combined to provide (Z)-3-aminotridec-2-en-4-one (2.9 mg, 47%) The product was typically immediately dissolved in anhydrous DMSO and was stored frozen. $^1$H-NMR (500 MHz, d6-DMSO) δ 5.53 (q, J=7.1 Hz, 1H); 4.31 (s, 2H); 2.60 (t, J=7.4 Hz, 2H); 1.65 (d, J=7.1 Hz, 3H); 1.51-1.43 (m, 2H); 1.29-1.16 (m, 12H); 0.85 (t, J=6.8 Hz, 3H). $^{13}$C-NMR (125 MHz, d6-DMSO) δ 197.1, 141.8, 106.7, 35.2, 31.3, 29.0, 28.9, 28.7 (2C), 25.0, 22.2, 14.0, 12.1. HRMS (ESI-TOF) 212.2010 [M+H]+(calculated for $C_{13}H_{26}NO$=212.2014).

(Z)-3-aminonon-2-en-4-one, 6. Prepared in an analogous manner to (Z)-3-aminotridec-2-en-4-one (Ea-CAI1) from (Z)-allyl (4-oxonon-2-en-3-yl)carbamate to provide (Z)-3-aminonon-2-en-4-one (4.7 mg, 66%). $^1$H-NMR (500 MHz, d6-DMSO) δ 5.53 (q, J=7.1 Hz, 1H); 4.31 (s, 2H); 2.61 (t, J=7.4 Hz, 2H); 1.65 (d, J=7.1 Hz, 3H); 1.48 (pentet, J=7.4 Hz, 2H); 1.33-1.14 (m, 4H); 0.85 (t, J=7.1 Hz, 3H). $^{13}$C-NMR (125 MHz, d6-DMSO) δ 197.1, 141.8, 106.7, 35.1, 30.9, 24.7, 22.0, 13.9, 12.1. HRMS (ESI-TOF) 156.1386 [M+H]$^+$ (calculated for $C_9H_{18}NO$=156.1388).

(Z)-3-aminodec-2-en-4-one, 7. Prepared in an analogous manner to (Z)-3-aminotridec-2-en-4-one (Ea-CAI1) from (Z)-allyl (4-oxodec-2-en-3-yl)carbamate to provide (Z)-3-aminodec-2-en-4-one (5.9 mg, 66%). $^1$H-NMR (500 MHz, d6-DMSO) δ 5.53 (q, J=7.1 Hz, 1H); 4.31 (s, 2H); 2.61 (t, J=7.4 Hz, 2H); 1.65 (d, J=7.1 Hz, 3H); 1.52-1.44 (m, 2H); 1.31-1.18 (m, 6H); 0.85 (t, J=6.8 Hz, 3H). $^{13}$C-NMR (125 MHz, d6-DMSO) δ 197.1, 141.8, 106.7, 35.1, 31.2, 28.4, 25.0, 22.1, 14.0, 12.1. HRMS (ESI-TOF) 170.1539 [M+H]$^+$ (calculated for $C_{10}H_{20}NO$=170.1545).

(Z)-3-aminoundec-2-en-4-one, 8. Prepared in an analogous manner to (Z)-3-aminotridec-2-en-4-one (Ea-CAI1) from (Z)-allyl (4-oxoundec-2-en-3-yl)carbamate to provide (Z)-3-aminoundec-2-en-4-one (3.9 mg, 34%). $^1$H-NMR (500 MHz, d6-DMSO) δ 5.53 (q, J=7.1 Hz, 1H); 4.31 (s, 2H); 2.61 (t, J=7.4 Hz, 2H); 1.65 (d, J=7.1 Hz, 3H); 1.51-1.43 (m, 2H); 1.30-1.18 (m, 8H); 0.85 (t, J=6.9 Hz, 3H). $^{13}$C-NMR (125 MHz, d6-DMSO) δ 197.1, 141.8, 106.7, 35.2, 31.2, 28.7, 28.6, 25.0, 22.1, 14.0, 12.1. HRMS (ESI-TOF) 184.1699 [M+H]$^+$ (calculated for $C_{11}H_{22}NO$=184.1701).

(Z)-3-aminododec-2-en-4-one, 9. Prepared in an analogous manner to (Z)-3-aminotridec-2-en-4-one (Ea-CAI1) from (Z)-allyl (4-oxododec-2-en-3-yl)carbamate to provide (Z)-3-aminododec-2-en-4-one (2.8 mg, 59%). $^1$H-NMR (500 MHz, d6-DMSO) δ 5.53 (q, J=7.1 Hz, 1H); 4.31 (s, 2H); 2.61 (t, J=7.4 Hz, 2H); 1.65 (d, J=7.1 Hz, 3H); 1.52-1.43 (m, 2H); 1.32-1.16 (m, 10H); 0.85 (t, J=6.8 Hz, 3H). $^{13}$C-NMR (125 MHz, d6-DMSO) δ 197.1, 141.8, 106.7, 35.2, 31.3, 28.9, 28.7, 28.7, 25.0, 22.1, 14.0, 12.1. HRMS (ESI-TOF) 198.1853 [M+H]$^+$ (calculated for $C_{12}H_{24}NO$=198.1858).

(Z)-3-aminotetradec-2-en-4-one, 10. Prepared in an analogous manner to (Z)-3-aminotridec-2-en-4-one (Ea-CAI1) from (Z)-allyl (4-oxotetradec-2-en-3-yl)carbamate to provide (Z)-3-aminotetradec-2-en-4-one (4.4 mg, 51%). $^1$H-NMR (500 MHz, d6-DMSO) δ 5.53 (q, J=7.1 Hz, 1H); 4.30 (s, 2H); 2.60 (t, J=7.4 Hz, 2H); 1.65 (d, J=7.1 Hz, 3H); 1.53-1.43 (m, 2H); 1.36-1.14 (m, 14H); 0.85 (t, J=6.8 Hz, 3H). $^{13}$C-NMR (125 MHz, d6-DMSO) δ 197.1, 141.8, 106.7, 35.2, 31.3, 29.0, 28.9, 28.8, 28.8, 28.7, 25.0, 22.2, 14.0, 12.1. HRMS (ESI-TOF) 226.2166 [M+H]$^+$ (calculated for $C_{14}H_{28}NO$=226.2171).

(Z)-3-aminohexadec-2-en-4-one, 11. Prepared in an analogous manner to (Z)-3-aminotridec-2-en-4-one (Ea-CAI1) from (Z)-allyl (4-oxohexadec-2-en-3-yl)carbamate to provide (Z)-3-aminohexadec-2-en-4-one (7.5 mg, 67%). $^1$H-NMR (500 MHz, d6-DMSO) δ 5.52 (q, J=7.1 Hz, 1H); 4.31 (s, 2H); 2.60 (t, J=7.4 Hz, 2H); 1.65 (d, J=7.1 Hz, 3H);

1.53-1.43 (m, 2H); 1.33-1.15 (m, 18H); 0.85 (t, J=6.8 Hz, 3H). $^{13}$C-NMR (125 MHz, d6-DMSO) δ 197.1, 141.8, 106.7, 35.2, 31.4, 29.2, 29.1, 29.0, 29.0, 28.9, 28.8, 28.7, 25.0, 22.2, 14.0, 12.1. HRMS (ESI-TOF) 254.2481 [M+H]$^+$ (calculated for $C_{16}H_{32}NO$=254.2484).

tert-butyl (2-oxoundecyl)carbonate. Prepared using a modification of a reported procedure.[2] To a solution of tert-Butyl (2-(methoxy(methyl)amino)-2-oxoethyl)carbamate (500 mg, 2.29 mmol) in THF (23 mL) at 0° C. was added nonyl-MgBr (1.0M in Et$_2$O, 11.5 mL, 11.5 mmol) and the mixture was allowed to stir at 0° C. for 4 h. The mixture was quenched with sat. NH$_4$Cl (50 mL), extract with Et$_2$O (2×50 mL), dry over Na$_2$SO$_4$ and concentrate in vacuo. The mixture was purified by silica gel chromatography (20% to 40% EtOAc/hexanes) to provide tert-butyl (2-oxoundecyl)carbonate as a clear colorless oil (510 mg, 78%). $^1$H-NMR (500 MHz, CDCl$_3$) δ 5.22 (s, 1H); 4.00 (d, J=4.7 Hz, 1H); 3.62 (m, 1H); 2.39 (t, J=7.5 Hz, 2H); 1.63-1.50 (m, 2H); 1.39 (s, 9H); 1.36-1.17 (m, 12H); 0.85 (t, J=7.0 Hz, 3H). $^{13}$C-NMR (125 MHz, CDCl$_3$) δ 206.2, 155.8, 79.9, 50.4, 40.3, 32.1, 29.5, 29.5, 29.5, 29.4, 28.5, 23.9, 22.9, 14.3.

3-methyl-5-nonylisoxazol-4-amine, 15. To a solution of acetaldehyde oxime (1 g, 16.9 mmol) in DMF (34 mL) at room temperature was added N-chloro succinimide (2.9 g, 21.9 mmol) and the mixture was allowed to stir for 3.5 h. The reaction was quenched with H$_2$O (40 mL), extracted with EtOAc (3×40 mL), dried over MgSO$_4$, filtered and concentrated in vacuo to yield N-hydroxyacetimidoyl chloride as a clear, colorless oil that was used without further purification. To tert-butyl (2-oxoundecyl)carbonate (510 mg, 1.78 mmol) in THF (3.6 mL) at −78° C. was added tert-butyl lithium (1.7M in pentane, 2.1 mL, 3.56 mmol). The resulting mixture was allowed to stir at −78° C. for 20 min and was treated with the above prepared N-hydroxyacetimidoyl chloride (166.4 mg, 1.78 mmol) as a solution in THF (1.8 mL). The resulting mixture was allowed to warm slowly to room temperature and was stirred at room temperature overnight. The reaction was quenched with sat. NH$_4$Cl (10 mL), extracted with Et$_2$O (3×10 mL), dried over Na$_2$SO$_4$ and concentrated in vacuo. The residue (300 mg) was dissolved in CH$_2$Cl$_2$ (9.3 mL) and H$_2$O (140 µL) at room temperature and was treated with TFA (700 µL, 9.25 mmol). The mixture was allowed to stir overnight, was concentrated to dryness and the residue was purified by silica gel chromatography (40% EtOAc/hexanes to 100% EtOAc) to yield 3-methyl-5-nonylisoxazol-4-amine as a yellow solid (48 mg, 12% over two steps). $^1$H-NMR (500 MHz, CDCl$_3$) δ 8.18 (bs, 2H); 2.72 (t, J=7.6 Hz, 2H); 2.25 (s, 3H); 1.69-1.55 (m, 2H); 1.34-1.15 (m, 12H); 0.86 (t, J=6.9 Hz, 3H). $^{13}$C-NMR (125 MHz, CDCl$_3$) δ 165.1, 155.2, 111.0, 32.0, 29.5, 29.4, 29.3, 29.3, 27.2, 25.0, 22.8, 14.2, 9.1. HRMS (ESI-TOF) 225.1961 [M+H]$^+$ (calculated for $C_{13}H_{25}N_2O$=225.1967).

4-methyl-3-nonylisoxazol-5-amine, 16. To a solution of decanal oxime[3] (2 g, 11.67 mmol) in CH$_2$Cl$_2$ (58 mL) at room temperature was added benzyltrimethylammonium tetrachloroiodate (4.89 g, 11.67 mmol) and the mixture was allowed to stir for 1 h before dilution with Et$_2$O (280 mL). The resulting precipitate was removed by filtration and the filtrate was concentrated to dryness to provide N-hydroxydecanimidoyl chloride which was used without further purification. To propionitrile (1.22 mL, 17.49 mmol) in THF (35 mL) at −78° C. was added tert-butyl lithium (1.7M in pentane, 10.3 mL, 17.5 mmol) and the mixture was allowed to react at −78° C. for 40 min before the addition of a solution of N-hydroxydecanimidoyl chloride (1.0M solution in Et$_2$O, 5.83 mL). The mixture was allowed to stir at −78° C. for 4 h. The reaction was quenched with sat. NH$_4$Cl (70 mL), extracted with Et$_2$O (3×70 mL), dried over Na$_2$SO$_4$ and concentrated in vacuo. The residue was purified by silica gel chromatography (40% EtOAc/hexanes to 100% EtOAc) to yield 4-methyl-3-nonylisoxazol-5-amine as a white solid (116 mg, 9% over two steps). $^1$H-NMR (500 MHz, CDCl$_3$) δ 4.16-4.05 (m, 2H); 2.47 (t, J=7.9 Hz, 2H); 1.76 (s, 3H); 1.66-1.54 (m, 2H); 1.41-1.17 (m, 12H); 0.87 (t, J=6.8 Hz, 3H). $^{13}$C-NMR (125 MHz, CDCl$_3$) δ 165.1, 164.5, 87.5, 32.0, 29.6, 29.5, 29.5, 27.6, 25.7, 22.8, 21.2, 14.3, 6.2. HRMS (ESI-TOF) 225.1966 [M+H]$^+$ (calculated for $C_{13}H_{25}N_2O$=225.1967).

General Procedure A. Synthesis of Acylated Pyrrole Analogs (Compounds 17, 18 and 21-35). To a solution of the pyrrole (1.0 eq) in Et$_2$O (1.4M) was added MeMgBr (1.0 eq) and the mixture is stirred at reflux for 30 minutes before cooling to 0° C. The cooled solution is treated with the appropriate acid chloride (1.0 eq) as a solution in PhMe (1.0M) and the mixture is allowed to warm slowly to room temperature and stirred overnight. The reaction is quenched with sat. NH$_4$Cl (double reaction volume), extracted with Et$_2$O (3× double reaction volume), dried over Na$_2$SO$_4$ and concentrated in vacuo before purification by silica gel chromatography. Both regioisomers of the acylated pyrrole are readily accessible in this manner. The 3-acylated pyrrole analogs typically eluted after the 2-acylated analogs.

1-(1H-pyrrol-2-yl)decan-1-one, 17. Prepared according to general procedure A to provide 1-(1H-pyrrol-2-yl)decan-1-one as an off-white solid (1.8 g, 28%). $^1$H-NMR (500 MHz, CDCl$_3$) δ 10.5 (s, 1H); 7.04 (s, 1H); 6.92 (s, 1H); 6.25 (s, 1H); 2.76 (t, J=7.5 Hz, 2H); 1.80-1.65 (m, 2H); 1.45-1.14 (m, 12H); 0.86 (t, J=6.8 Hz, 3H). $^{13}$C-NMR (125 MHz, CDCl$_3$) δ 191.8, 132.1, 125.3, 116.7, 110.5, 38.2, 32.0, 29.6, 29.5, 25.6, 22.8, 14.3. HRMS (ESI-TOF) 222.1852 [M+H]$^+$ (calculated for $C_{14}H_{24}NO$=222.1858).

1-(1H-pyrrol-3-yl)decan-1-one, 18. Prepared according to general procedure A to provide 1-(1H-pyrrol-2-yl)decan-1-one as an off-white solid (1.3 g, 20%). $^1$H-NMR (500 MHz, CDCl$_3$) δ 9.32 (s, 1H); 7.41 (s, 1H); 6.76 (s, 1H); 6.63 (s, 1H); 2.73 (t, J=7.6 Hz, 2H); 1.75-1.62 (m, 2H); 1.39-1.12 (m, 12H); 0.85 (t, J=6.8 Hz, 3H). $^{13}$C-NMR (125 MHz, CDCl$_3$) δ 197.7, 126.0, 123.6, 119.8, 108.8, 40.0, 32.1, 29.7, 29.7, 29.5, 25.4, 22.9, 14.3. HRMS (ESI-TOF) 222.1854 [M+H]$^+$ (calculated for $C_{14}H_{24}NO$=222.1858).

1-(2,5-dimethyl-1H-pyrrol-3-yl)decan-1-one, 19. To a solution of 2,5-dimethyl pyrrole (500 µL, 4.91 mmol) in CH$_2$Cl$_2$ (5 mL) at 0° C. was added decanoyl chloride (1.0 mL, 4.91 mmol). Aluminum (III) chloride (654.7 mg, 4.91 mmol) was added portion wise to the resulting solution and the mixture was allowed to stir at 0° C. for 1 h. The mixture was quenched by the addition of sat. NaHCO$_3$ (10 mL), extracted with CH$_2$Cl$_2$ (3×10 mL), dried over Na$_2$SO$_4$ and concentrated in vacuo. The residue was purified by silica gel chromatography (hexanes to 40% EtOAc/hexane) to provide 1-(2,5-dimethyl-1H-pyrrol-3-yl)decan-1-one (153 mg, 13%). $^1$H-NMR (500 MHz, CDCl$_3$) δ 7.90 (s, 1H); 6.17 (s, 1H); 2.68 (t, J=7.6 Hz, 2H); 2.51 (s, 3H); 2.22 (s, 3H); 1.71-1.59 (m, 2H); 1.39-1.18 (m, 12H); 0.87 (t, J=6.8 Hz, 3H). $^{13}$C-NMR (125 MHz, CDCl$_3$) δ 198.0, 134.0, 125.4, 120.6, 107.6, 40.6, 31.9, 29.7, 29.7, 29.7, 29.5, 24.9, 22.7, 14.3, 14.1, 12.8. HRMS (ESI-TOF) 250.2161 [M+H]$^+$ (calculated for $C_{16}H_{28}NO$=250.2171).

1(2,4-dimethyl-1H-pyrrol-3-yl)decan-1-one, 20. To a solution of 2,4-dimethyl pyrrole (500 µL, 4.91 mmol) in CH$_2$Cl$_2$ (5 mL) at 0° C. was added decanoyl chloride (1.0 mL, 4.91 mmol). Aluminum (III) chloride (654.7 mg, 4.91 mmol) was added portion wise to the resulting solution and the mixture was allowed to stir at 0° C. for 1 h. The mixture was quenched by the addition of sat. NaHCO$_3$ (10 mL), extracted with CH$_2$Cl$_2$ (3×10 mL), dried over Na$_2$SO$_4$ and concentrated in vacuo. The residue was purified by silica gel chromatography (hexanes to 40% EtOAc/hexane) to provide 1-(2,4-dimethyl-1H-pyrrol-3-yl)decan-1-one as an off white solid (82 mg, 7%). $^1$H-NMR (500 MHz, CDCl$_3$) δ 7.85 (s, 1H); 6.17 (s, 1H); 2.68 (t, J=7.5 Hz, 2H); 2.51 (s, 3H); 2.22 (s, 3H); 1.72-1.60 (m, 2H); 1.39-1.18 (m, 12H); 0.87 (t, J=6.7 Hz, 3H). $^{13}$C-NMR (125 MHz, CDCl$_3$) δ 197.9, 134.0, 125.3, 120.6, 107.6, 40.6, 32.0, 29.7, 29.7, 29.7, 29.5, 24.9, 22.7, 14.3, 14.1, 12.8. HRMS (ESI-TOF) 250.2160 [M+H]$^+$ (calculated for C$_{16}$H$_{28}$NO=250.2171).

1-(1H-pyrrol-3-yl)hexan-1-one, 21. Prepared according to general procedure A to provide 1-(1H-pyrrol-3-yl)hexan-1-one as an off-white solid (387 mg, 16%). $^1$H-NMR (500 MHz, CDCl$_3$) δ 8.55 (s, 1H); 7.41 (s, 1H); 6.76 (s, 1H); 6.65 (s, 1H); 2.73 (t, J=7.6 Hz, 2H); 1.76-1.64 (m, 2H); 1.38-1.28 (m, 4H); 0.87 (t, J=6.7 Hz, 3H). $^{13}$C-NMR (125 MHz, CDCl$_3$) δ 197.0, 126.3, 123.0, 119.4, 109.1, 40.0, 31.9, 24.9, 22.8, 14.2. HRMS (ESI-TOF) 166.1232 [M+H]$^+$ (calculated for C$_{10}$H$_{16}$NO=166.1232).

1-(1H-pyrrol-3-yl)heptan-1-one, 22. Prepared according to general procedure A to provide 1-(1H-pyrrol-3-yl)heptan-1-one as an off-white solid (121 mg, 5%). $^1$H-NMR (500 MHz, CDCl$_3$) δ 8.71 (s, 1H); 7.41 (s, 1H); 6.96 (s, 1H); 6.65 (s, 1H); 2.73 (t, J=7.6 Hz, 2H); 1.74-1.56 (m, 2H); 1.39-1.18 (m, 6H); 0.86 (t, J=6.9 Hz, 3H). $^{13}$C-NMR (125 MHz, CDCl$_3$) δ 197.1, 126.2, 123.2, 119.5, 109.0, 40.0, 31.9, 29.4, 25.2, 22.8, 14.3. HRMS (ESI-TOF) 180.1384 [M+H]$^+$ (calculated for C$_{11}$H$_{18}$NO=180.1388).

1-(1H-pyrrol-3-yl)octan-1-one, 23. Prepared according to general procedure A to provide 1-(1H-pyrrol-3-yl)octan-1-one as an off-white solid (92 mg, 33%). $^1$H-NMR (500 MHz, CDCl$_3$) δ 8.47 (s, 1H); 7.41 (s, 1H); 6.76 (s, 1H); 6.65 (s, 1H); 2.72 (t, J=7.4 Hz, 2H); 1.73-1.57 (m, 2H); 1.38-1.17 (m, 8H); 0.85 (t, J=6.8 Hz, 3H). $^{13}$C-NMR (125 MHz, CDCl$_3$) δ 196.7, 126.4, 123.0, 119.4, 109.1, 40.0, 32.0, 29.7, 29.4, 25.3, 22.9, 14.3. HRMS (ESI-TOF) 194.1545 [M+H]$^+$ (calculated for C$_{12}$H$_{20}$NO=194.1545).

1-(1H-pyrrol-3-yl)nonan-1-one, 24. Prepared according to general procedure A to provide 1-(1H-pyrrol-3-yl)nonan-1-one as an off-white solid (431 mg, 14%). $^1$H-NMR (500 MHz, CDCl$_3$) δ 9.32 (s, 1H); 7.41 (s, 1H); 6.76 (s, 1H); 6.63 (s, 1H); 2.73 (t, J=7.4 Hz, 2H); 1.75-1.62 (m, 2H); 1.39-1.12 (m, 10H); 0.85 (t, J=6.8 Hz, 3H). $^{13}$C-NMR (125 MHz, CDCl$_3$) δ 196.7, 126.0, 123.6, 119.7, 108.8, 40.0, 32.0, 29.7, 29.7, 29.5, 25.4, 22.9, 14.3. HRMS (ESI-TOF) 208.1703 [M+H]$^+$ (calculated for C$_{13}$H$_{22}$NO=208.1701).

1-(1H-pyrrol-3-yl)dodecan-1-one, 25. Prepared according to general procedure A to provide 1-(1H-pyrrol-3-yl)dodecan-1-one as an off-white solid (108 mg, 3%). $^1$H-NMR (500 MHz, CDCl$_3$) δ 8.50 (s, 1H); 7.41 (s, 1H); 6.77 (s, 1H); 6.65 (s, 1H); 2.72 (t, J=7.4 Hz, 2H); 1.73-1.62 (m, 2H); 1.37-1.16 (m, 16H); 0.85 (t, J=6.7 Hz, 3H). $^{13}$C-NMR (125 MHz, CDCl$_3$) δ 196.9, 126.3, 123.0, 119.4, 109.1, 40.0, 32.1, 29.9, 29.8, 29.7, 29.6, 25.2, 22.9, 14.4. HRMS (ESI-TOF) 250.2167 [M+H]$^+$ (calculated for C$_{16}$H$_{28}$NO=250.2171).

3-(4-butylphenyl)-1-(1H-pyrrol-3-yl)propan-1-one, 26. Prepared according to general procedure A to provide 3-(4-butylphenyl)-1-(1H-pyrrol-3-yl)propan-1-one as an off-white solid (62.7 mg, 4%) $^1$H-NMR (500 MHz, CDCl$_3$) δ 8.55 (s, 1H), 7.42-7.41 (m, 1H), 7.17-7.09 (m, 4H), 6.78-6.77 (m, 1H), 6.68-6.67 (m, 1H), 3.09-3.06 (m, 2H), 3.02-2.99 (m, 2H), 2.57 (t, J=7.8 Hz, 2H), 1.61-1.55 (m, 4H), 1.39-1.31 (m, 2H), 0.93-0.91 (t, J=7.3 Hz, 3H). $^{13}$C-NMR (125 MHz, CDCl$_3$) δ 195.4, 140.7, 139.0, 128.5, 128.3, 126.0, 123.0, 119.4, 109.0, 41.8, 35.4, 33.9, 30.3, 22.5, 14.1. HRMS (ESI-TOF) 256.1701 [M+H]+(calculated for C$_{17}$H$_{22}$NO=256.1701).

3-(4-butylphenyl)-1-(1H-pyrrol-2-yl)propan-1-one, 27. Prepared according to general procedure A to provide 3-(4-butylphenyl)-1-(1H-pyrrol-2-yl)propan-1-one as an off-white solid (190.3 mg, 11%) $^1$H-NMR (500 MHz, CDCl$_3$) δ 9.60 (s, 1H), 7.17-7.10 (m, 4H), 7.03-7.02 (m, 1H), 6.91-6.90 (m, 1H), 6.28-6.26 (m, 1H), 3.12-3.07 (m, 2H), 3.04-3.00 (m, 2H), 2.58 (t, J=7.77, 2H), 1.62-1.56 (m, 2H), 1.39-1.32 (m, 2H), 0.93 (t, J=7.35, 3H). $^{13}$C-NMR (125 MHz, CDCl$_3$) δ 190.0, 140.8, 138.5, 132.0, 128.7, 128.3, 124.7, 116.3, 110.8, 39.9, 35.4, 33.9, 30.5, 22.5, 14.1. HRMS (ESI-TOF) 256.1701 [M+H]$^+$ (calculated for C$_{17}$H$_{22}$NO=256.1701).

7-phenyl-1-(1H-pyrrol-3-yl)heptan-1-one, 28. Prepared according to general procedure A to provide 7-phenyl-1-(1H-pyrrol-2-yl)heptan-1-one as an off-white solid (69.8 mg, 3%) $^1$H-NMR (500 MHz, CDCl$_3$) δ 8.67 (s, 1H), 7.42-7.41 (m, 1H), 7.29-7.25 (m, 2H), 7.19-7.15 (m, 3H), 6.79-6.77 (dd, J=2.4 Hz, 1H), 6.67-6.66 (dd, J=2.6, 1.5 Hz, 1H), 2.74 (t, J=7.5 Hz, 2H), 2.59 (t, J=7.8 Hz, 2H), 1.74-1.68 (m, 2H), 1.65-1.59 (m, 2H), 1.42-1.33 (m, 4H). $^{13}$C-NMR (125 MHz, CDCl$_3$) δ 197.4, 142.9, 128.5, 128.3, 125.8, 125.7, 123.5, 119.7, 108.7, 39.8, 36.0, 31.5, 29.4, 29.2, 25.1. HRMS (ESI-TOF) 256.1700 [M+H]+(calculated for C$_{17}$H$_{22}$NO=256.1701).

7-phenyl-1-(1H-pyrrol-2-yl)heptan-1-one, 29. Prepared according to general procedure A to provide 7-phenyl-1-(1H-pyrrol-2-yl)heptan-1-one as an off-white solid (267 mg, 13%) $^1$H-NMR (500 MHz, CDCl$_3$) δ 9.48 (s, 1H), 7.32-7.28 (m, 2H), 7.22-7.19 (m, 3H), 7.05-7.04 (m, 1H), 6.93-6.92 (m, 1H), 6.31-6.29 (m, 1H), 2.78 (t, J=7.5 Hz, 2H), 2.63 (t, J=7.7 Hz, 2H), 1.77-1.70 (m, 2H), 1.68-1.62 (m, 2H), 1.46-1.36 (m, 4H). $^{13}$C-NMR (125 MHz, CDCl$_3$) δ 191.2, 142.9, 132.2, 128.5, 128.4, 125.7, 124.4, 116.1, 110.7, 38.1, 36.0, 31.5, 29.4, 29.2, 25.3. HRMS (ESI-TOF) 256.1713 [M+H]$^+$ (calculated for C$_{17}$H$_{22}$NO=256.1701).

3-(4-butylphenyl)-1-(1H-pyrrol-3-yl)prop-2-en-1-one, 30. Prepared according to general procedure A to provide 3-(4-butylphenyl)-1-(1H-pyrrol-3-yl)prop-2-en-1-one as an off-white solid (62.7 mg, 4%) $^1$H-NMR (500 MHz, CDCl$_3$) δ 8.73 (s, 1H), 7.78 (d, J=15.6 Hz, 1H), 7.59 (s, 1H), 7.54 (d, J=7.8 Hz, 2H), 7.27 (d, J=15.6 Hz, 1H), 7.21 (d, J=7.7 Hz, 2H), 6.83 (d, J=14.2, 2H), 2.63 (t, J=7.7 Hz, 2H), 1.64-1.58 (m, 2H), 1.36 (h, J=7.4 Hz, 2H), 0.93 (t, J=7.3 Hz, 3H). $^{13}$C-NMR (125 MHz, CDCl$_3$) δ 185.25, 145.60, 142.31, 132.77, 129.09, 128.48, 127.00, 123.69, 122.70, 119.74, 109.40, 35.74, 33.59, 22.50, 14.11. HRMS (ESI-TOF) 254.1554 [M+H]$^+$ (calculated for C$_{17}$H$_{20}$NO=254.1545).

3-(4-butylphenyl)-1-(1H-pyrrol-2-yl)prop-2-en-1-one, 31. Prepared according to general procedure A to provide 3-(4-butylphenyl)-1-(1H-pyrrol-2-yl)prop-2-en-1-one as an off-white solid (18.6 mg, 5%) $^1$H-NMR (500 MHz, CDCl$_3$) δ 10.86 (s, 1H), 7.94 (d, J=15.7 Hz, 1H), 7.63 (d, J=8.3 Hz, 2H), 7.44 (d, J=15.7 Hz, 1H), 7.29 (d, J=8.3 Hz, 2H), 7.24-7.23 (m, 1H), 7.20-7.18 (m, 1H), 6.44-6.41 (m, 1H), 2.70 (t, J=7.9 Hz, 2H), 1.70-1.65 (m, 2H), 1.43 (h, J=7.3 Hz, 2H), 1.01 (t, J=7.5 Hz, 3H). $^{13}$C-NMR (125 MHz, CDCl$_3$) δ 179.14, 145.84, 142.55, 133.28, 132.53, 129.11, 128.48, 125.75, 121.03, 116.55, 111.03, 35.72, 33.54, 22.46, 14.08. HRMS (ESI-TOF) 254.1564 [M+H]$^+$ (calculated for C$_{17}$H$_{20}$NO=254.1545).

(E)-1-(1H-pyrrol-3-yl)dec-2-en-1-one, 32. Prepared according to general procedure A to provide (E)-1-(1H-pyrrol-3-yl)dec-2-en-1-one as an off-white solid (14.6 mg, 1%) ¹H-NMR (500 MHz, CDCl₃) δ 8.64 (s, 1H), 7.49 (m, 1H), 7.05-6.99 (dt, J=15.3, 7.0 Hz, 1H), 6.81-6.78 (m, 1H), 6.75-6.73 (m, 1H), 6.68-6.64 (dt, J=15.3, 1.5 Hz, 1H), 2.29-2.24 (m, 2H), 1.51-1.46 (m, 2H), 1.29-1.26 (m, 8H), 0.89-0.83 (m, 3H). ¹³C-NMR (125 MHz, CDCl₃) δ 185.6, 147.0, 127.0, 126.6, 123.5, 119.6, 109.4, 32.8, 31.9, 29.4, 29.3, 28.5, 22.8, 14.3. HRMS (ESI-TOF) 220.1700 [M+H]⁺ (calculated for $C_{14}H_{22}NO=220.1701$).

(E)-1-(1H-pyrrol-2-yl)dec-2-en-1-one, 33. Prepared according to general procedure A to provide (E)-1-(1H-pyrrol-2-yl)dec-2-en-1-one as an off-white solid (42.1 mg, 2%). ¹H-NMR (500 MHz, CDCl₃) δ 10.13 (s, 1H), 7.13-7.07 (m, 2H), 6.98-6.96 (m, 1H), 6.73 (d, J=15.6, 1H), 6.31-6.29 (m, 1H), 2.32-2.27 (m, 2H), 1.54-1.48 (m, 2H), 1.38-1.23 (m, 8H), 0.89 (t, J=6.7 Hz, 3H). ¹³C-NMR (125 MHz, CDCl₃) δ 179.5, 147.5, 132.8, 125.4, 116.5, 110.8, 32.8, 32.0, 29.4, 29.2, 28.4, 22.8, 14.2. HRMS (ESI-TOF) 220.1723 [M+H]⁺ (calculated for $C_{14}H_{22}NO=220.1701$).

2-([1,1'-biphenyl]-4-yl)-1-(1H-pyrrol-3-yl)ethanone, 34. Prepared according to general procedure A to provide 2-([1,1'-biphenyl]-4-yl)-1-(1H-pyrrol-3-yl)ethanone as an off-white solid (13.4 mg, 2%) ¹H-NMR (500 MHz, CDCl₃) δ 8.60 (s, 1H), 7.59-7.53 (m, 4H), 7.49-7.48 (m, 1H), 7.44-7.40 (m, 2H), 7.38-7.31 (m, 3H), 6.79-6.78 (m, 1H), 6.73-6.72 (m, 1H), 4.10 (s, 2H). ¹³C-NMR (125 MHz, CDCl₃) δ 193.4, 141.0, 139.7, 134.7, 129.9, 128.9, 127.4, 127.2, 125.7, 123.8, 119.6, 109.5, 46.6. HRMS (ESI-TOF) 262.1228 [M+H]⁺ (calculated for $C_{18}H_{16}NO=262.1232$).

2-([1,1'-biphenyl]-4-yl)-1-(1H-pyrrol-2-yl)ethanone, 35. Prepared according to general procedure A to provide 2-([1,1'-biphenyl]-4-yl)-1-(1H-pyrrol-2-yl)ethanone as an off-white solid (175 mg, 20%) ¹H-NMR (500 MHz, CDCl₃) δ 9.60 (s, 1H), 7.58-7.54 (m, 4H), 7.45-7.32 (m, 4H), 7.36-7.32 (m, 1H), 7.06-7.04 (dd, J=4.5, 2.5 Hz, 2H), 6.32-6.30 (m, 1H), 4.11 (s, 2H). ¹³C-NMR (125 MHz, CDCl₃) δ 187.8, 141.0, 139.9, 134.2, 131.7, 129.9, 128.9, 127.5, 127.3, 127.2, 125.1, 117.1, 111.1, 44.6. HRMS (ESI-TOF) 262.1235 [M+H]⁺ (calculated for $C_{18}H_{16}NO=262.1232$).

REFERENCES

[1] A. Afzali-Ardakani, H. Rapoport, *J. Org. Chem.* 1980, 45, 4817-4820.
[2] J. Liu, N. Ikemoto, D. Petrillo, J. D. Armstrong III, *Tetrahedron Letters* 2002, 43, 8223-8226.
[3] A. C. Biraboneye, S. Madonna, P. Maher, J.-L. Kraus, *Chem Med Chem* 2010, 5, 79-85.
[4] D. H. Lenz, K. C. Mok, B. N. Lilley, R. V. Kulkarni, N. S. Wingreen, B. L. Bassler, *Cell* 2004, 118, 69-82.
[5] D. A. Higgins, M. E. Pomianek, C. M. Kraml, R. K. Taylor, M. F. Semmelhack, B. L. Bassler, *Nature* 2007, 450, 883-886.
[6] ICCVAM. 2006a. Background Review Document: In Vitro Cytotoxicity Test Methods for Estimating Acute Oral Systemic Toxicity. NIH Publication No. 07-4518. Research Triangle Park, N.C.: National Institute of Environmental Health Sciences. Available Aug. 13, 2013: http://iccvam.niehs.nih.gov/.

Various modifications and variations of the invention in addition to those shown and described herein will be apparent to those skilled in the art without departing from the scope and spirit of the invention and fall within the scope of the appended claims. Although the invention has been described in connection with specific preferred embodiments, it should be understood that the invention as claimed should not be unduly limited to such specific embodiments. All publications and patents mentioned in the above specification are incorporated in their entirety by reference.

The invention claimed is:

1. A 3-acyl pyrrole compound having one of the structures of the group consisting of:

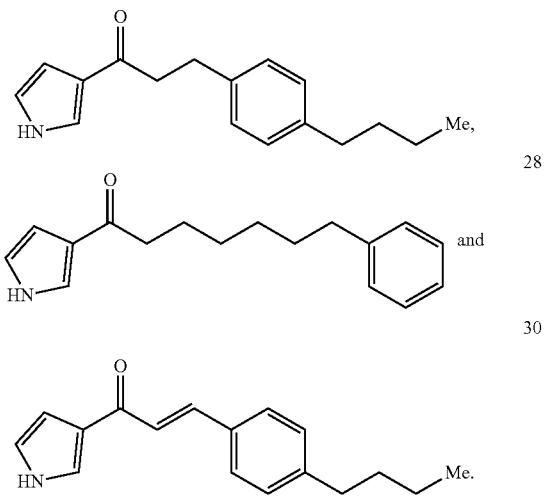

2. A pharmaceutical composition comprising one or more compounds of claim 1 and a pharmaceutically acceptable carrier, excipient or diluent.

3. A bacterial biofilm-inhibiting composition comprising two or more compounds of claim 1.

4. A device that is coated or embedded with one or more compounds of claim 1 to prevent bacterial biofilm formation or bacterial transmission.

* * * * *